(12) United States Patent
Organ et al.

(10) Patent No.: US 6,768,921 B2
(45) Date of Patent: Jul. 27, 2004

(54) ELECTRICAL IMPEDANCE METHOD AND APPARATUS FOR DETECTING AND DIAGNOSING DISEASES

(75) Inventors: Leslie W. Organ, Charleston, SC (US); Kenneth C. Smith, Toronto (CA); Reza Safaee-Rad, Etobicoke (CA); Milan Graovac, Toronto (CA); George P. Darmos, Willowdale (CA); Ilya Gavrilov, Richmond Hill (CA)

(73) Assignee: Z-Tech (Canada) Inc., Toronto (CA)

( * ) Notice: Subject to any disclaimer, the term of this patent is extended or adjusted under 35 U.S.C. 154(b) by 84 days.

(21) Appl. No.: 09/749,613

(22) Filed: Dec. 28, 2000

(65) Prior Publication Data

US 2002/0123694 A1 Sep. 5, 2002

(51) Int. Cl.[7] .................................................. A61B 5/05
(52) U.S. Cl. ........................................ 600/547; 600/300
(58) Field of Search ......................... 600/300, 372–395, 600/517

(56) References Cited

U.S. PATENT DOCUMENTS

| | | | |
|---|---|---|---|
| 4,034,854 A | | 7/1977 | Bevilacqua |
| 4,291,708 A | | 9/1981 | Frei et al. |
| 4,365,634 A | | 12/1982 | Bare et al. |
| 4,407,300 A | | 10/1983 | Davis |
| 4,458,694 A | | 7/1984 | Sollish et al. |
| 4,486,835 A | | 12/1984 | Bai et al. |
| 4,537,203 A | * | 8/1985 | Machida ................ 600/547 |
| 4,539,640 A | | 9/1985 | Fry et al. |
| 4,557,271 A | * | 12/1985 | Stoller et al. ............. 600/547 |
| 4,583,549 A | | 4/1986 | Manoli |
| 4,617,939 A | | 10/1986 | Brown et al. |
| 4,688,580 A | | 8/1987 | Ko et al. |
| 4,763,660 A | | 8/1988 | Kroll et al. |
| 4,942,880 A | | 7/1990 | Slövak |
| 5,143,079 A | | 9/1992 | Frei et al. |
| 5,311,878 A | | 5/1994 | Brown et al. |
| 5,372,141 A | * | 12/1994 | Gallup .................... 600/547 |
| 5,465,730 A | | 11/1995 | Zadehkoochak et al. |
| 5,544,662 A | | 8/1996 | Saulnier et al. |

(List continued on next page.)

FOREIGN PATENT DOCUMENTS

| | | |
|---|---|---|
| CA | 2231038 | 11/1999 |
| FR | 2 486 386 | 1/1982 |

OTHER PUBLICATIONS

Pethig, R., and Kell, D.B., The Passive Electrical Properties of Biological Systems: Their Significance in Physiology, Biophysics and Biotechnology, *Phys. Med. Biol.* 32:933–970, 1987.

(List continued on next page.)

*Primary Examiner*—Charles Marmor
(74) *Attorney, Agent, or Firm*—McDermott Will & Emery LLP

(57) ABSTRACT

The present invention relates to an improved method and apparatus for detecting and diagnosing disease states in a living organism by using a plurality of electrical impedance measurements. In particular, the invention provides for an improved electrode array for diagnosing the presence of a disease state in the human breast, and discloses a method of application of the array to the breast that ensures that the multiplicity of impedance measurements obtained from a first body part correspond as precisely and reproducibly as possible to the multiplicity of impedance measurements that are obtained from another, homologous, second body part. A number of diagnostic methods based on homologous electrical difference analysis are disclosed, including the calculation of a number of metrics used to indicate disease states by comparison with pre-established threshold values, and the construction of a number of graphical displays for indicating the location of disease to a body part sector.

38 Claims, 18 Drawing Sheets

U.S. PATENT DOCUMENTS

| | | | |
|---|---|---|---|
| 5,588,429 A | | 12/1996 | Isaacson et al. |
| 5,704,355 A | | 1/1998 | Bridges |
| 5,746,214 A | | 5/1998 | Brown et al. |
| 5,807,251 A | * | 9/1998 | Wang et al. ................ 600/407 |
| 5,810,742 A | * | 9/1998 | Pearlman ................... 600/547 |
| 5,919,142 A | | 7/1999 | Boone et al. |
| 6,122,544 A | * | 9/2000 | Organ |

OTHER PUBLICATIONS

Chaudhary, S.S., Mishra, R.K., Swarup, A., and Thomas, J.M., Dielectric Properties of Normal & Malignant Human Breast Tissues at Radiowave and Microwave Frequencies, *Indian J. Biochem. Biophys.* 21:76–79, 1984.

Surowiec, A.J., Stuchly, S.S., Barr, J.R., and Swarup, A., Dielectric Properties of Breast Carcinoma and the Surrounding Tissues, *IEEE Trans. Biomed. Engng.* 35:257–263, 1988.

Jossinet, J. Fourcade, C., and Schmitt, M., A Study for Breast Imaging with a Circular Array of Impedance Electrodes, *Proc. Vth Int. Conf. Biolectrical Impedance*, 1981, Tokyo, Japan, 83–86.

Jossinet, J.C., and Mbock–Mbock, E., Technical Implementation and Evaluation of a Bioelectrical Breast Scanner, *Proc. 10th Int. Conf. IEEE Engng. Med. Biol.*, 1988, New Orleans, USA (Imped. Imaging II).

Skidmore, R., Evans, J.M., Jenkins, D., and Wells, P.N.T., A Data Collection System for Gathering Electrical Impedance Measurements from the Human Breast, *Clin. Phs. Physio. Meas.*, 8:99–102, 1987.

Piperno, G., Frei, E.H., and Moshitzky, M., Breast Cancer Screening by Impedance Measurements, *Front. Med. Biol. Engng*, 2:111–117, 1990.

Man, B., Sollish, B.D., Moshitzky, M. Choukron, Y., and Frei, E.H., Results of Preclinical Tests for Breast Cancer Detection by Dielectric Measurements, *XII Int. Conf. Med. Biol. Engng.*, 1979, Jerusalem, Israel. Springer Int., Berlin, 1980, 30.4.

Sollish, B.D., Frei, E.H., Hammerman, E., Lang, S.B., and Moshitzky, M., Microprocessor–assisted Screening Techniques. Isr. J. Med. Sci. 17:859–864, 1981.

* cited by examiner

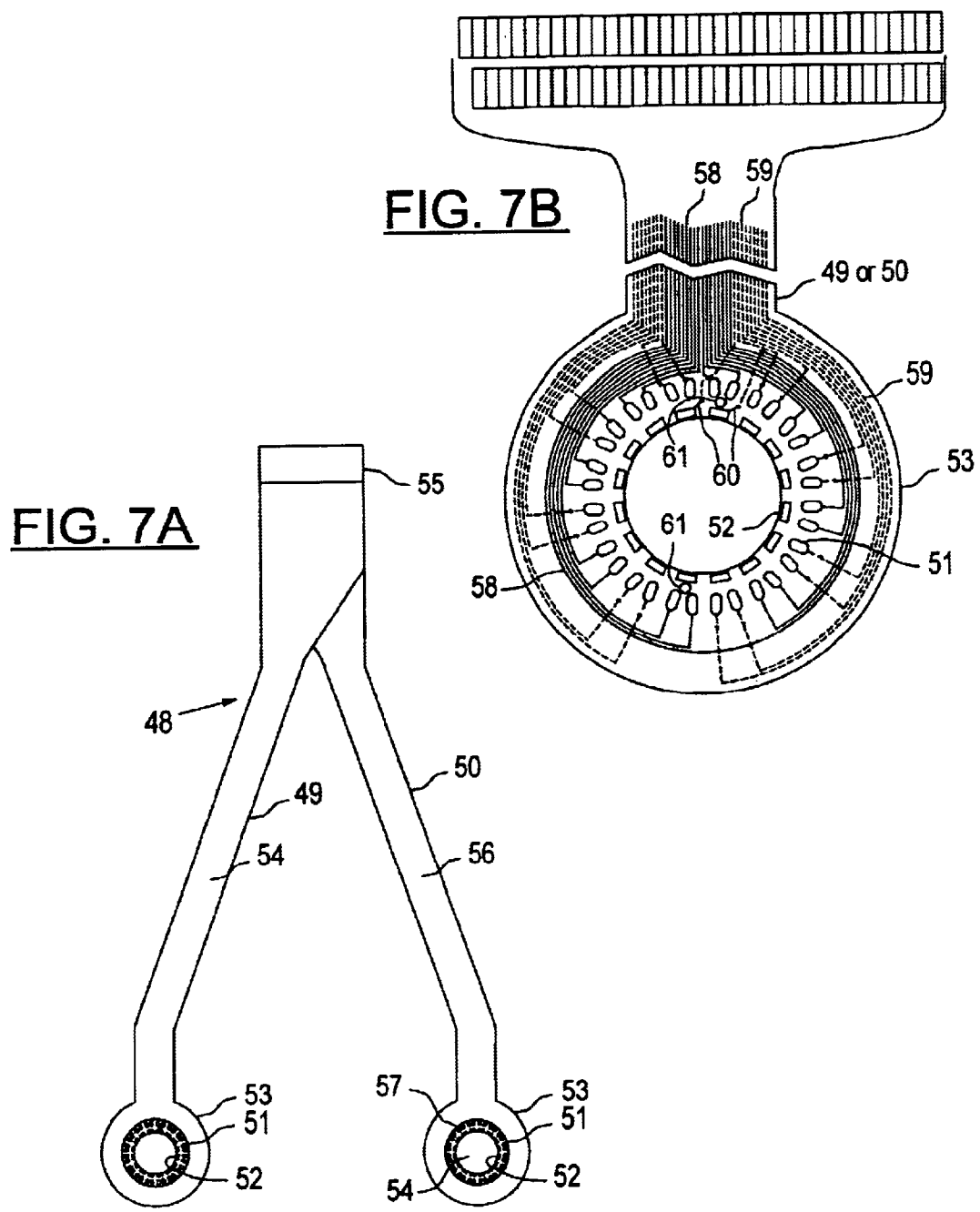

135

136

ELECTRICAL IMPEDANCE METHOD AND APPARATUS FOR DETECTING AND DIAGNOSING DISEASES

FIELD OF THE INVENTION

The present invention relates to an improved method and apparatus for detecting and diagnosing disease states in a living organism by using a plurality of electrical impedance measurements.

BACKGROUND OF THE INVENTION

Methods for screening and diagnosing diseased states within the body are based on sensing a physical characteristic or physiological attribute of body tissue, and then distinguishing normal from abnormal states from changes in the characteristic or attribute. For example, X-ray techniques measure tissue physical density, ultrasound measures acoustic density, and thermal sensing techniques measures differences in tissue heat. Another measurable property of tissue is its electrical impedance; i.e., the resistance tissue offers to the flow of electrical current through it. Values of electrical impedance of various body tissues are well known through studies on intact humans or from excised tissue made available following therapeutic surgical procedures. In addition, it is well documented that a decrease in electrical impedance occurs in tissue as it undergoes cancerous changes. This finding is consistent over many animal species and tissue types, including, for example human breast cancers.

There have been a number of reports of attempts to detect breast tumors using electrical impedance imaging, such as, for example, U.S. Pat. No. 4,486,835. However, there are basic problems when trying to construct an image from impedance data. Electrical current does not proceed in straight lines or in a single plane; it follows the path of least resistance, which is inevitably irregular and three-dimensional. As a result, the mathematics for constructing the impedance image is very complex and requires simplifying assumptions that greatly decrease image fidelity and resolution.

A cancer, however, need not be "seen" to be detected; its presence can be detected by a marker associated with it, in this case a change in its electrical impedance, and a technique sensitive to the marker.

One technique for screening and diagnosing diseased states within the body using electrical impedance is disclosed in U.S. Pat. No. 6,122,544. In this patent data are obtained in organized patterns from two anatomically homologous body regions, one of which may be affected by disease. One subset of the data so obtained is processed and analyzed by structuring the data values as elements of an n×n impedance matrix. The matrices can be further characterized by their eigenvalues and eigenvectors. These matrices and/or their eigenvalues and eigenvectors can be subjected to a pattern recognition process to match for known normal or disease matrix or eigenvalue and eigenvectors patterns. The matrices and/or their eigenvalues and eigenvectors derived from each homologous body region can also be compared, respectively, to each other using various analytical methods and then subject to criteria established for differentiating normal from diseased states.

SUMMARY OF THE PRESENT INVENTION

The present invention is directed to an improved method and apparatus for detecting and diagnosing disease states in a living organism by using a plurality of electrical impedance measurements. Although the present invention can be applied to any two homologous body regions, the application discussed scans for the presence or absence of breast abnormalities, and particularly benign and malignant tumors. While not intending to be bound by any particular theory, the method of the invention may arise from the following assumptions and hypotheses:

1. The tumor or tumors will occur either in only one breast, or if in both, at different homologous locations;
2. Both breasts are structurally similar, and therefore can be expected to be approximate mirror images (homologous) with respect to their impedance characteristics;
3. If impedance measurements are taken in a multiplicity of directions or paths across the breast (called an impedance scan in the present application), the presence of tumors, which are known to have a significantly lower impedance than the normal tissue they replace, will distort or change the impedance in at least some of the paths of current flow;
4. The magnitude of decreased impedance is greater for malignant tumors than for benign ones, providing a method for differentiating between these tumor types; and
5. There will always be some differences in impedance between breasts in a normal individual; but these differences will be less than the differences when a cancer is present.

The methodology of the present invention is implemented by a data acquisition and analysis apparatus that was developed for the special requirements of the invention. An improved breast electrode array is also provided of a design and construction that allows excellent conformability of the array to a breast surface and precise positioning of electrodes. This ensures that the multiplicity of positions that impedance measurements are obtained from in a first body part correspond as precisely as possible to the multiplicity of positions that measurements are obtained from in another, homologous, second body part. The apparatus has a number of innovations that provide rapid, accurate impedance measurements from a large number of electrode combinations, and virtually immediate data analysis and display. Impedance data are obtained in organized patterns from two anatomically homologous body regions, one of which may be affected by disease.

In one embodiment of the invention, electrodes are selected so that the impedance data obtained can be considered to represent elements of an n×n impedance matrix. Then two matrix differences are calculated to obtain a diagnostic metric from each. In one, the absolute difference between homologous right and left matrices, on an element-by-element basis, is calculated; in the second, the same procedure is followed except relative matrix element difference is calculated.

In another embodiment of the invention, the differences between corresponding impedance readings in the two body parts are compared in variety of ways that allow the calculation of metrics that can serve either as an indicator of the presence of disease or localize the disease to a specific breast quadrant or sector. Impedance differences are also displayed in a circular pixel plot in a representation of the frontal plane of the breast in this disclosure, although other shape plots in the same or other planes could effectively be produced with suitable choice of electrode geometry and positioning. The use of impedance differences subtracts out a voluminous and complex amount of impedance data produced by irregular, three-dimensional current paths, since under generally normal circumstances, the paths can be expected to be substantially identical in both body parts. Remaining differences are assumed to be due to disease states, and are much more manageable analytically.

Whereas the illustrated example of the present invention is a novel and improved method and apparatus for detecting and locating breast cancers, the invention can also be applied to other diseases or conditions in which there is a distinguishable difference in electrical impedance in the tissue as a result of the disease or condition. The present invention can also be used for detecting and locating diseases or conditions in any region of the body in which the electrical impedance of the region containing the disease or condition can be compared to an essentially identical, normal body region; for example, right and left forearms, right and left thighs, or right and left calves. Moreover, the present invention can be used to detect and locate diseases or conditions in any region of the body in which the electrical impedance of the region containing the disease or condition can be compared to another normal body region that, while not entirely identical, is consistently and constantly different; for example, right and left sides of the abdomen. In other words, the differences between the two regions being compared is a known constant in a healthy person and therefore can be subtracted out when performing a comparison.

In particular, this invention provides for an electrode array for diagnosing the presence of a disease state in a living organism, wherein the electrode array comprises a flexible body, a plurality of flexible arms extending from the body, and a plurality of electrodes provided by the plurality of flexible arms, wherein the electrodes are arranged on the arms to obtain impedance measurements between respective electrodes. In a preferred embodiment the plurality of flexible arms are spaced around the flexible body and are provided with an electrode pair.

Moreover, the flexible body of the electrode array can be provided with a stiffening member adapted to flatten part of the tissue of the living organism being diagnosed. In a preferred embodiment of the invention, the stiffening member is in the form of a ring and includes adhesive for fixation to the skin.

Further, each electrode of the electrode array can comprise an adhesive for fixation to the skin. In a preferred embodiment the adhesive is hydrogel. In another embodiment the adhesive is a gel foam pad, and particularly a gel foam pad in the form of a well that is filled with hydrogel.

The electrode array can also include means extending at least partially between the electrodes to at least partially electrically isolate the electrodes from each other. In a preferred embodiment the means comprises a ground conductive path. Moreover, the plurality of electrodes can comprise electrode pairs with each electrode pair having a current electrode and a voltage electrode. In this embodiment, the ground conductive path can extend at least partially between the current electrode and voltage electrode. Further, each electrode is connected to an associated terminal by a conductive path and the ground conductive path can extend at least partially between the conductive paths and associated terminals of respective electrodes to at least partially electrically isolate the conductive paths and the terminals from each other.

A method of forming an electrode array from a plurality of electrode array elements is also disclosed. Each electrode array element comprises a body having at least one arm extending from the body with at least one electrode provided on the arm. The method comprises:

a) overlying the plurality of electrode array elements at the respective bodies thereof to form a main body of the electrode array with the arms of the respective electrode array elements extending from the main body in spaced relation; and b) clamping the plurality of electrode array elements together.

An alignment means can be provided to ensure that the arms of the respective electrode array elements extend around the main body of the electrode array in spaced relation. Moreover, a retaining member is used to clamp the plurality of electrode array elements together, and the retaining member can comprise a stiffening member.

This invention also provides a method of confirming whether an electrode array for use in diagnosing a part of a living organism has been properly connected to an electronic module. The electrode array includes a conductive path and a connector to link the conductive path to the electronic module. The method comprises attaching the conductive path to a terminal of the connector, connecting the electrode array to the electronic module using the connector, and testing whether the conductive path is properly connected to the terminals of the connector. In the embodiment disclosed the conductive path is a ground loop.

This invention also provides for a template for positioning an electrode array on a part of a living organism to be diagnosed for the presence of a disease state. The template comprises a body having a plurality of spaced parallel lines, and at least two alignment marks positioned on the plurality of spaced parallel lines. The body can be comprised of a flexible and transparent material. Moreover, the body can be elongate in a direction perpendicular to the parallel lines and have at least one line extending perpendicular to the parallel lines. The template preferably has at least two alignment marks positioned on the line extending perpendicular to the parallel lines. The body of the template can present an opening through which at least a portion of the part of the living organism to be diagnosed is visible. The alignment marks can be spaced around the opening.

A method of positioning an electrode array on a part of a living organism using the template is also disclosed. The method comprises:

a) marking the living organism on or near the part to be diagnosed with a line;

b) placing the positioning template on the part to be diagnosed and aligning at least one of the spaced parallel lines to the line marked on the living organism;

c) marking on the living organism the location of the alignment marks of the template; and d) positioning the electrode array on the part to be diagnosed by aligning its corresponding alignment marks to the markings on the living organism from the template.

The invention also discloses a connecting member for connecting the electrode array to a connector that electrically links the electrode array to an electronic module. The connector member comprises a retaining member to receive the electrode array and connector in electrical contact with respect to one another, and a clamping member to clamp the electrode array and connector together and secure the electrical contact therebetween. The clamping member comprises a compressive member to apply a compressive force to the electrode array and connector. The retaining member comprises a base and a projection extending from the base over which a portion of the electrode array and connector can fit. The clamping member can further include a washer to fit over the projection of the retaining member and engage the electrode array and connector. The base of the retaining member can include at least one ridge extending from the base to engage the electrode array and connector on the opposite side from the washer. In the preferred embodiment the projection is a threaded tube and the compressive member is a fastening nut. Moreover, the base can further comprise alignment pins to ensure that the electrode array and connector are in correct electrical contact with respect to one another.

The washer can be provided with at least one channel adapted to fit therewithin the respective concentric ridges extending from the base. In one of the embodiments disclosed the washer is provided with at least two channels with each channel adapted to fit therewithin at least one of the ridges extending from the base. In another embodiment the washer is provided with at least two concentric ridges spaced to fit the respective concentric ridges extending from the base therebetween.

A method of connecting the electrode array to the connector that electrically links the electrode array to the electronic module is also disclosed. The method comprises:

a) placing the electrode array and connector in electrical contact with respect to one another; and b) clamping the electrode array and connector together to secure the electrical contact therebetween.

Moreover, a method of minimizing the number of connections in a conductive path of the electrode array and the connector is disclosed. The method comprises:

a) providing a plurality of spaced unlinked conducting surfaces on the electrode array;

b) providing a plurality of spaced unlinked conducting surfaces on the connector, with two of the conducting surfaces selected to be connected to the conductive path; and c) placing the electrode array and connector in electrical contact with respect to one another by overlapping the spaced unlinked conductive surfaces of the electrode array with the spaced unlinked conductive surfaces of the connector to form a continuous conductive path between the two selected conducting surfaces.

In a preferred embodiment the spaced unlinked conducting surfaces on the electrode array are spaced generally around an opening provided by the array, and the spaced unlinked conducting surfaces on the connector are spaced around a similar opening provided by the connector. The two selected conducting surfaces of the connector are adjacent to one another and a gap is provided in the spacing of the unlinked conducting surfaces of the electrode array so that when the electrode array and connector are placed in overlapping relation the gap is positioned with respect to the adjacent selected conducting surfaces of the connector so that the continuous path does not extend directly therebetween. In the preferred embodiment an alignment means is provided to ensure that the electrode array and connector overlie to form a continuous conductive path between the two selected conducting surfaces. Moreover, in the embodiment disclosed the conductive path is a ground conductive path.

Further, a method is disclosed for confirming an operable electrical contact between a plurality of spaced unlinked conducting surfaces of an electrode array and a plurality of spaced unlinked conducting surfaces of a connector. The method comprising:

a) placing the electrode array and connector in electrical contact with respect to one another by overlapping the spaced unlinked conductive surfaces of the electrode array with the spaced unlinked conductive surfaces of the connector to form a continuous conductive path between two selected conducting surfaces; and b) measuring a test signal over the conductive path between the two selected conducting surfaces to see if an operable electrical contact has been established.

In the embodiment disclosed the conductive path is a ground conductive path and electrical resistance is measured and compared to a pre-established value for an operable electrical contact. Moreover, placing the electrode array and connector in electrical contact with respect to one another places respective terminals for electrodes of the electrode array into electrical contact with respective conductive surfaces of the connector. The test establishes whether proper electrical contact between the respective terminals and conductive surfaces has been established.

Further, this invention discloses apparatus for obtaining and processing impedance measurements from an electrode array comprising means to connect the apparatus to the electrode array (for example, a multiplexer), means to control the connection means to produce a sequence of impedance measurements (for example, a multiplexer controller), computer means to control the sequence controlling means, and means connected to the computer means to display the impedance measurements and any analyses thereof. In a preferred embodiment the apparatus further comprises at least one EEPROM chip containing a selection pattern to produce the sequence of impedance measurements and a counter to sequence the multiplexer through the set of impedance measurements. The display can comprise display screen to provide monitoring of the impedance measurements and analyses thereof, or a printer for hard copy of the impedance measurements and analyses thereof.

In the embodiment disclosed each impedance measurement is displayed as a grid element. Means are provided to identify the corresponding electrodes of the electrode array used to obtain the impedance measurement represented by a given grid element. Moreover, the identifying means can be used to provide a value of the impedance measurement represented by the grid element. In addition, the display can be provided with means to indicate that the value of the impedance measurement represented by the grid element does not correspond to a predetermined expected value.

A method of testing a multiplexer of this invention using two substantially identical multiplexers is also disclosed. The method reversely operates one of the multiplexers. The method comprises:

a) connecting the respective outputs of the two multiplexers to one another;

b) providing a calibration load to the input of the reversely operating multiplexer;

c) simultaneously controlling operation of the two multiplexers through a sequence of identical output selections; and d) measuring the calibration load through the input of the normally operating multiplexer.

In particular, the measurement of the calibration load is an impedance measurement.

This invention also provides for a number of methods for diagnosing the possibility of a disease state in one of first and second substantially similar parts of a living organism. One method comprises:

a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;

b) identifying the set with a lower mean impedance value;

c) creating an absolute difference set by subtracting each measurement of the set with the lower mean impedance value from the corresponding measurement of the other set; and d) analyzing the absolute difference set to diagnose the possibility of a disease state.

In the embodiment disclosed each of the first and second sets are arranged in respective mathematical matrices, and the absolute difference set is an absolute difference matrix. The absolute difference matrix can be used to calculate a matrix norm that is compared to a pre-established threshold to diagnose the possibility of a disease state. The absolute difference matrix can also be used to calculate a matrix determinant that is compared to a pre-established threshold to diagnose the possibility of a disease state. Moreover, a sum of all of the elements in the absolute difference matrix can be calculated and compared to a pre-established threshold to diagnose the possibility of a disease state.

A visual display for diagnosing the possibility of a disease state and its location can also be provided by obtaining a sum of the values in each of the absolute difference matrix columns, then representing these sums in a graph, for example, as bar heights in a 2D graph. Another visual display can be obtained for diagnosing the possibility of a disease states and its location by plotting the value of each element in the absolute difference matrix as a function of the location of the value in the matrix. Such a plot can be in 3D.

Another method of diagnosing the possibility of a disease state in one of first and second substantially similar parts of a living organism comprises:

a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;

b) creating a relative difference set by calculating the relative differences between each measurement from the first set with the corresponding measurement of the second set; and c) analyzing the relative difference set to diagnose the possibility of a disease state.

Again, each of the first and second sets can be arranged in respective mathematical matrices, and the relative difference set is an relative difference matrix. The relative difference matrix can be used in a similar manner as the absolute difference matrix to diagnose the possibility of a disease state.

A further method comprises:

a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;

b) calculating an impedance range by subtracting the minimum impedance measurement from either of the first and second sets from the maximum impedance measurement from such sets;

c) creating a plurality of numbered bin by subdividing the impedance range into smaller range sizes, then numbering the smaller range sizes consecutively;

d) assigning a bin number to each of the impedance measurements from the first and second sets;

e) creating a bin difference set by subtracting the bin number of each impedance measurement from one of the first and second sets from the bin number of each corresponding impedance measurement of the other set; and f) analyzing the bin difference set to diagnose the possibility of a disease state.

In this method, a sum of all of the bin difference values in the bin difference set is calculated and compared to a pre-established threshold to diagnose the possibility of a disease state.

A similar method comprises:

a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;

b) calculating a first impedance range for the first set by subtracting the minimum impedance measurement from the maximum impedance measurement of that set, and calculating a second impedance range for the second set by subtracting the minimum impedance measurement from the maximum impedance measurement of that set;

c) creating a plurality of first numbered bins by subdividing the first impedance range into a first set of smaller range sizes, then numbering the first set of smaller range sizes consecutively, and creating a plurality of second numbered bins by subdividing the second impedance range into a second set of smaller of range sizes, then numbering the second set of smaller range sizes consecutively;

d) assigning one of the first bin numbers to each of the impedance measurements from the first set, and assigning one of the second bin numbers to each of the impedance measurements from the second set;

e) creating a bin difference set by subtracting the bin number of each impedance measurement from one of the first and second sets from the bin number of each corresponding impedance measurement of the other set; and f) analyzing the bin difference set to diagnose the possibility of a disease state.

In the embodiment disclosed a sum of all of the bin difference values in the bin difference set is calculated and compared to a pre-established threshold to diagnose the possibility of a disease state.

Yet a further method of diagnosing the possibility of a disease state in one of first and second substantially similar parts of a living organism comprises:

a) obtaining a plurality of impedance measurements taken between a predetermined plurality of points encircling the parts to produce first and second sets of impedance measurements, the first set for the first part and the second set for the second part, and wherein each measurement of the first set has a corresponding measurement in the second set when taken between a corresponding plurality of points;

b) assigning a bin number to each of the impedance measurements from the first and second sets;

c) producing a bin chord plot for each of the parts by graphically depicting the plurality of points as nodes on an encircling path for each part and the impedance measurements taken between the plurality of points as a chord extending between the respective nodes;

c) dividing each graphical depiction encircling each part into sectors; and d) analyzing the bin chords that converge on a given node within a sector to diagnose the possibility of a disease state.

In the embodiment disclosed each sector graphically displays the total number of bin chords that converge on all the nodes included within that sector. Moreover, in the preferred embodiment the difference between corresponding bin chords for each part is plotted as a bin difference chord on the graphical depiction for the part having a lower bin number. The calculation of the number of bin difference chords that converge on a given node is then weighted depending on the differences between bin numbers from the first set and corresponding bin numbers from the second set.

Yet a further method of diagnosing the possibility of a disease state in one of first and second substantially similar parts of a living organism is disclosed. The method comprises:

a) obtaining a plurality of impedance measurements taken between a predetermined plurality of points encircling the parts to produce first and second sets of impedance measurements, the first set for the first part and the second set for the second part, and wherein each measurement of the first set has a corresponding measurement in the second set when taken between a corresponding plurality of points;

b) producing a pixel grid from a chord plot produced by the impedance measurements taken between the plurality of points; and c) analyzing the pixel grid to diagnose the possibility of a disease state.

For this method the intensity of a pixel in the pixel grid is determined from the chords that pass through the pixel, i.e., by the number of chords that pass through the pixel, the size of the segments of the chords that pass through the pixels, and the impedance values of the chords that pass through the pixels. The intensity of the pixels can be equalized to account for differences in the number of chords that can pass through the various pixels and the size of the segments of the chords that pass through the pixels. Once equalized the pixel intensity indicates only impedance value.

Moreover, a pixel difference set can be created by subtracting the pixel impedance value from one of the first and second sets from the pixel impedance value of each corresponding pixel of the other set. In this method, a sum of all of the difference values in the pixel difference set is calculated and compared to a pre-established threshold to diagnose the possibility of a disease state.

The intensity of the pixels is displayed visually and can be generated by a computer to produce a plurality of levels that represent different impedance values. In a preferred embodiment the visual display generated by the computer has 256 intensity levels for representing different impedance values.

The pixel grid can be a pixel algebraic difference plot derived by subtracting corresponding impedance pixel measurements taken between the plurality of points of the first part and the second part. Further, the pixel grid can be a pixel relative difference plot derived by calculating the relative difference between corresponding impedance pixels from the plurality of points of the first and second part.

Further, for either pixel algebraic difference plots or for pixel relative difference plots the range of pixel impedance intensity can be scaled with a scale factor, derived for algebraic difference plots and for relative difference plots, pre-established such that the scale factor for the respective plot types, when applied to a subject having maximum observed pixel difference, would result in the maximum pixel intensity level of 256.

Yet further, for either pixel algebraic difference plots or for pixel relative difference plots the pixel grid can be divided into sectors with each sector graphically displaying the sum of the impedance values for all pixels that are within the sector.

BRIEF DESCRIPTION OF THE DRAWING FIGURES

For a better understanding of the present invention and to show more clearly how it may be carried into effect, reference will now be made, by way of example, to the accompanying drawings, which show a preferred embodiment of the present invention and in which:

FIG. 7A is an illustration of a flexible ribbon cable for electrical connection to the breast electrode array of FIG. 5;

Figure 1:
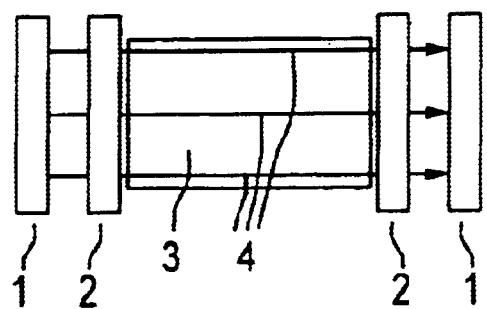
FIG. 1 is an illustration of a four electrode impedance measurement technique.
Figure 2:
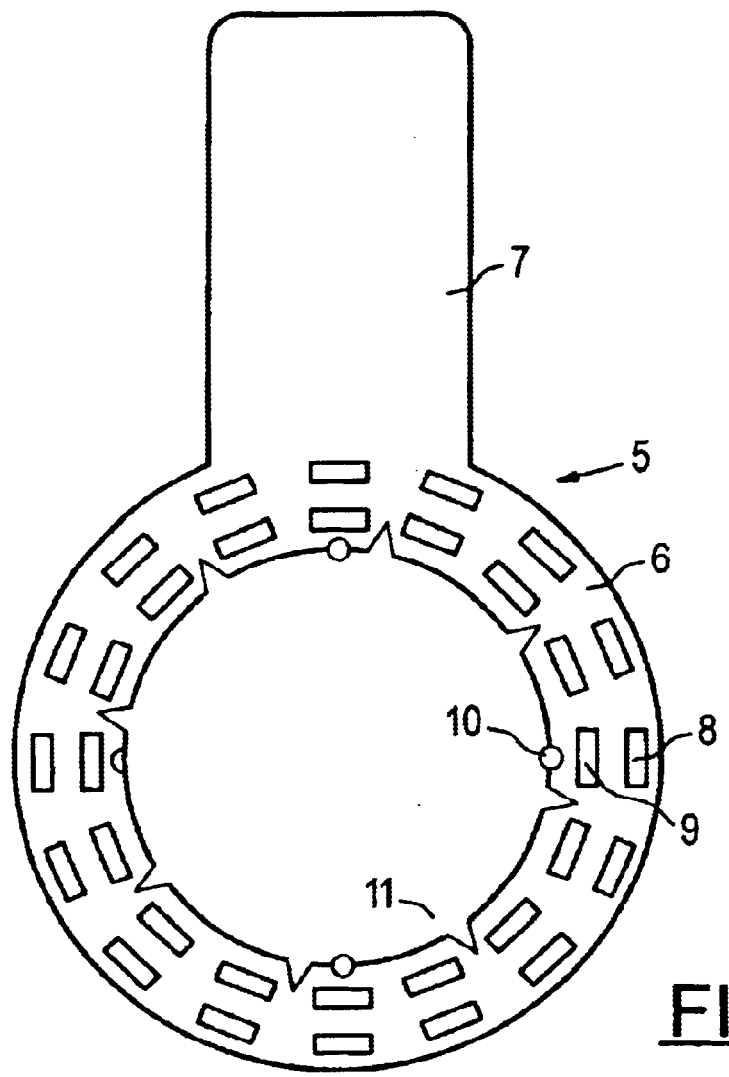
FIG. 2 is an illustration of one embodiment of a breast electrode array.
Figure 5:
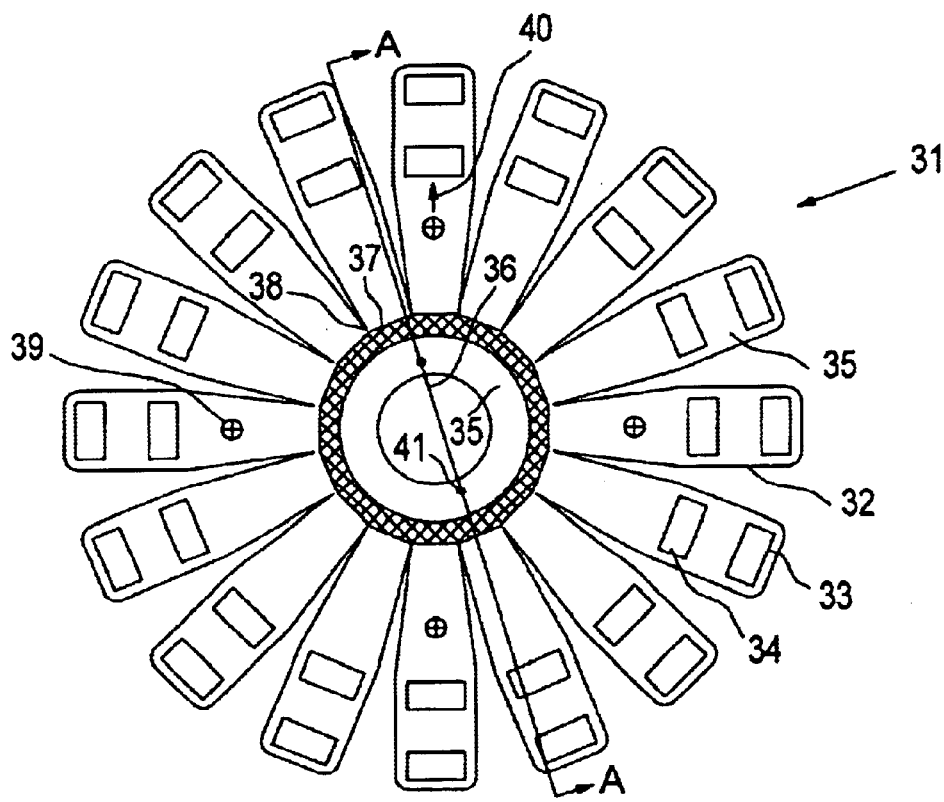
FIG. 5 is an illustration of an alternative embodiment of the breast electrode array of the invention.
Figure 8:
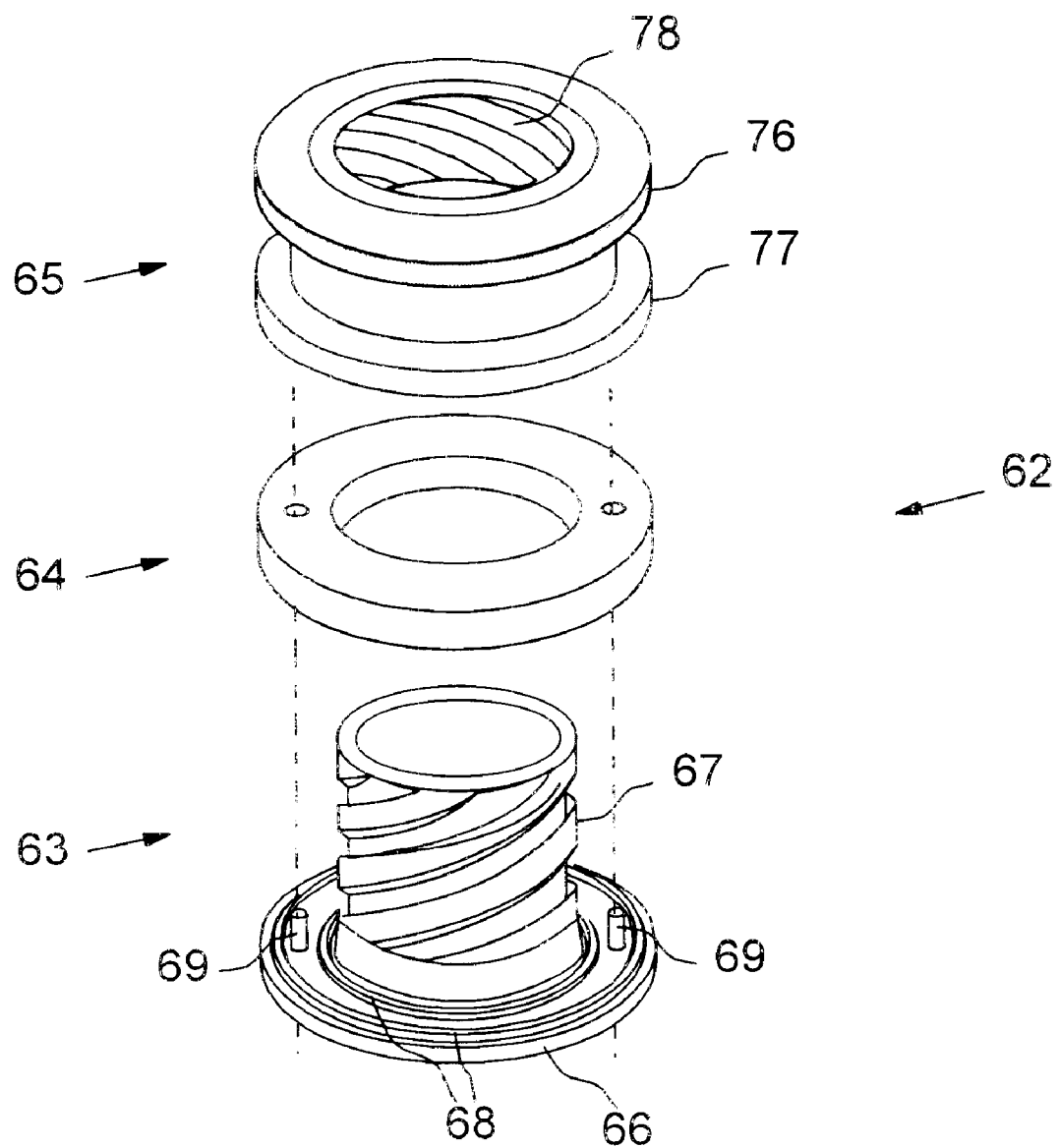
Figures 1, 9A:
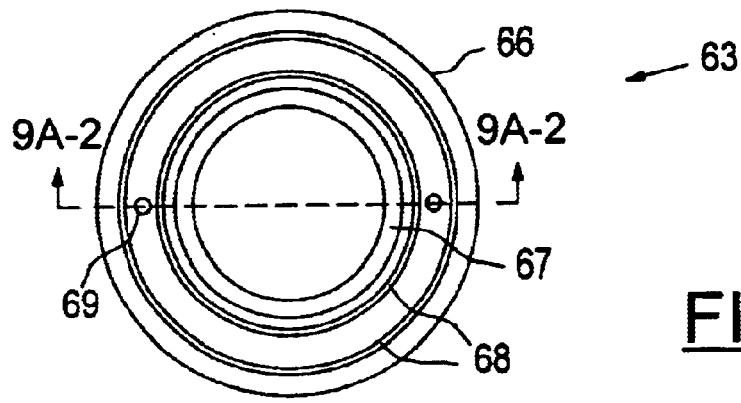
Figures 2, 9A:
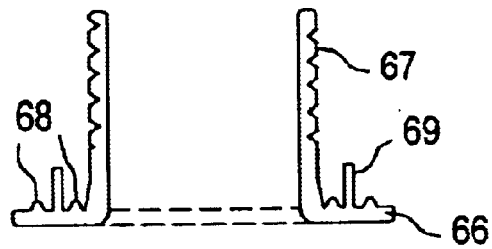
Figures 1, 9B:
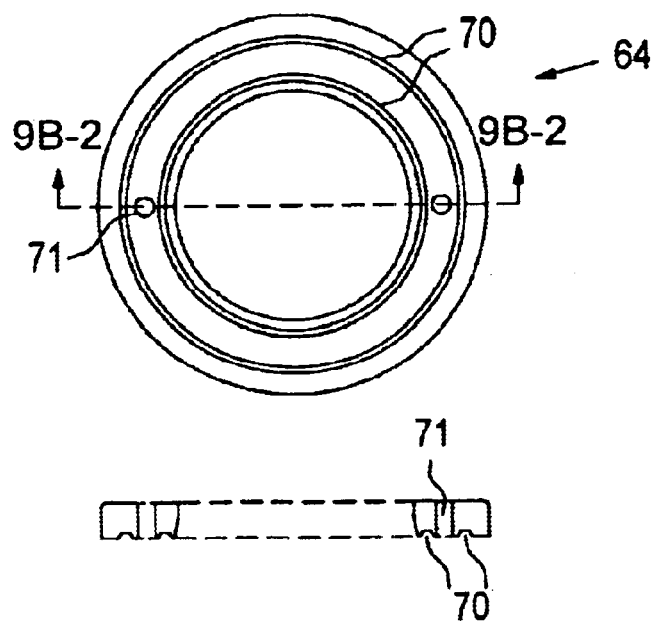
Figures 2, 9B:
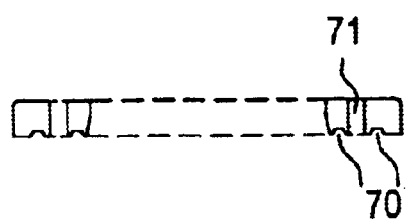
Figures 1, 9C:
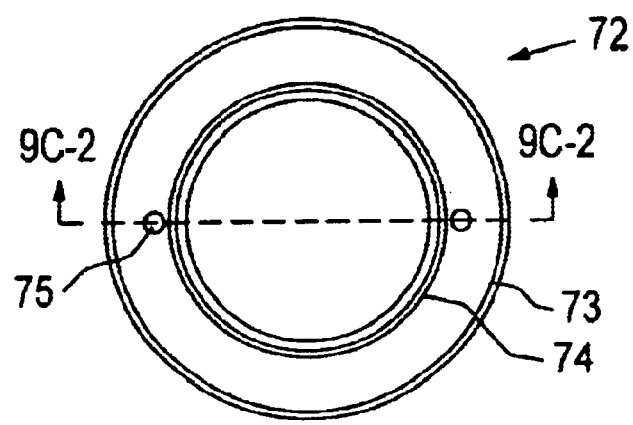
Figures 2, 9C:
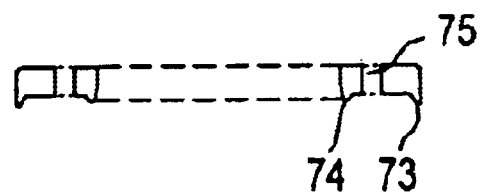
Figure 9D:
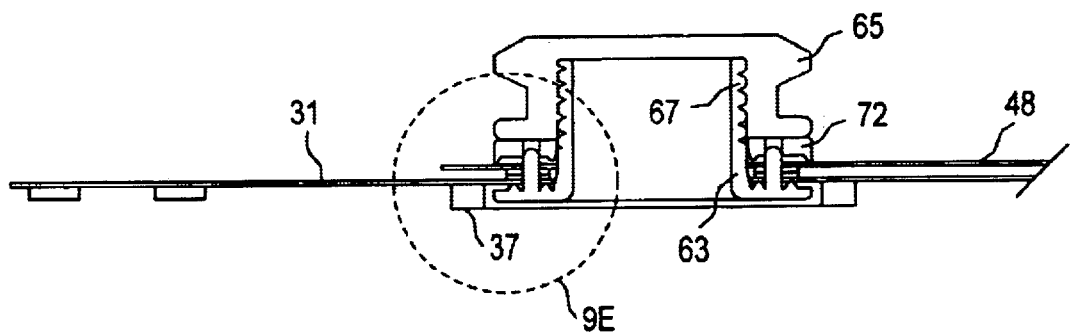
Figure 9E:
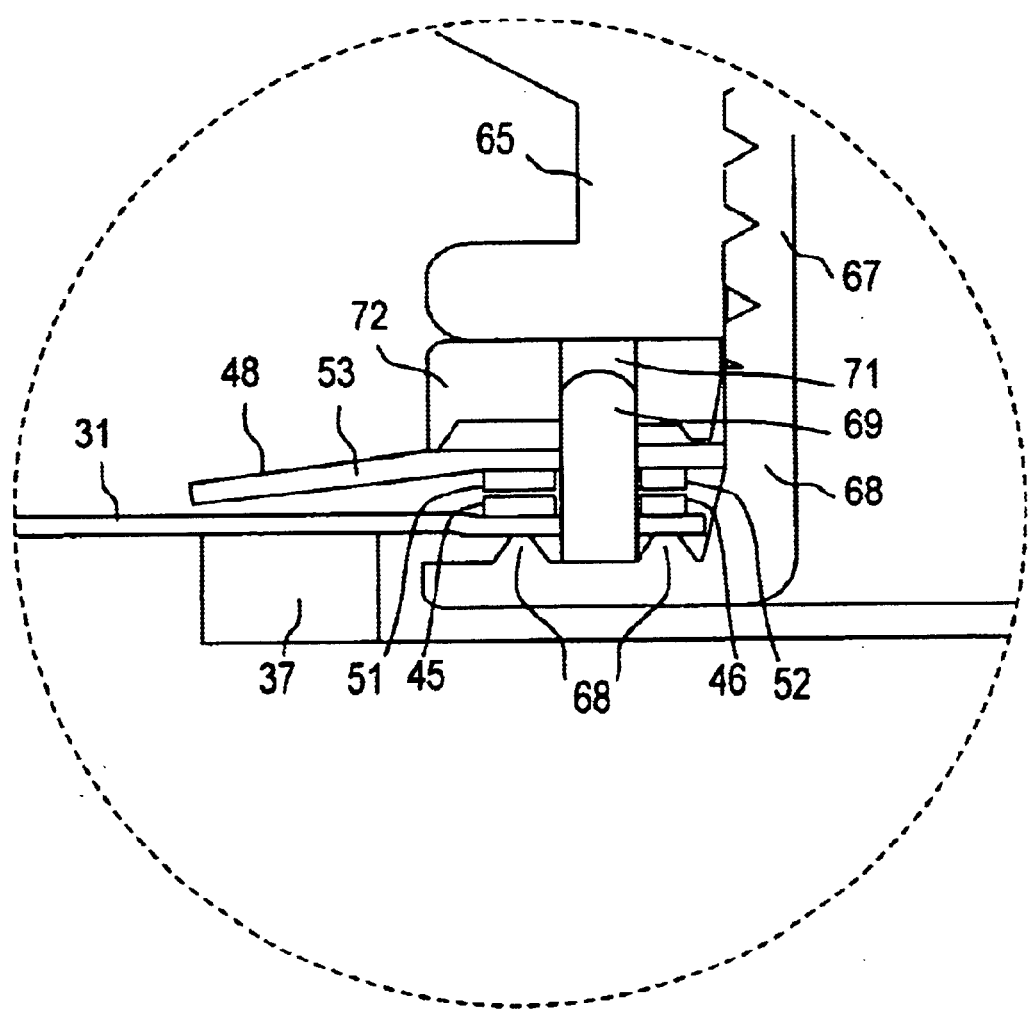
Figure 10:
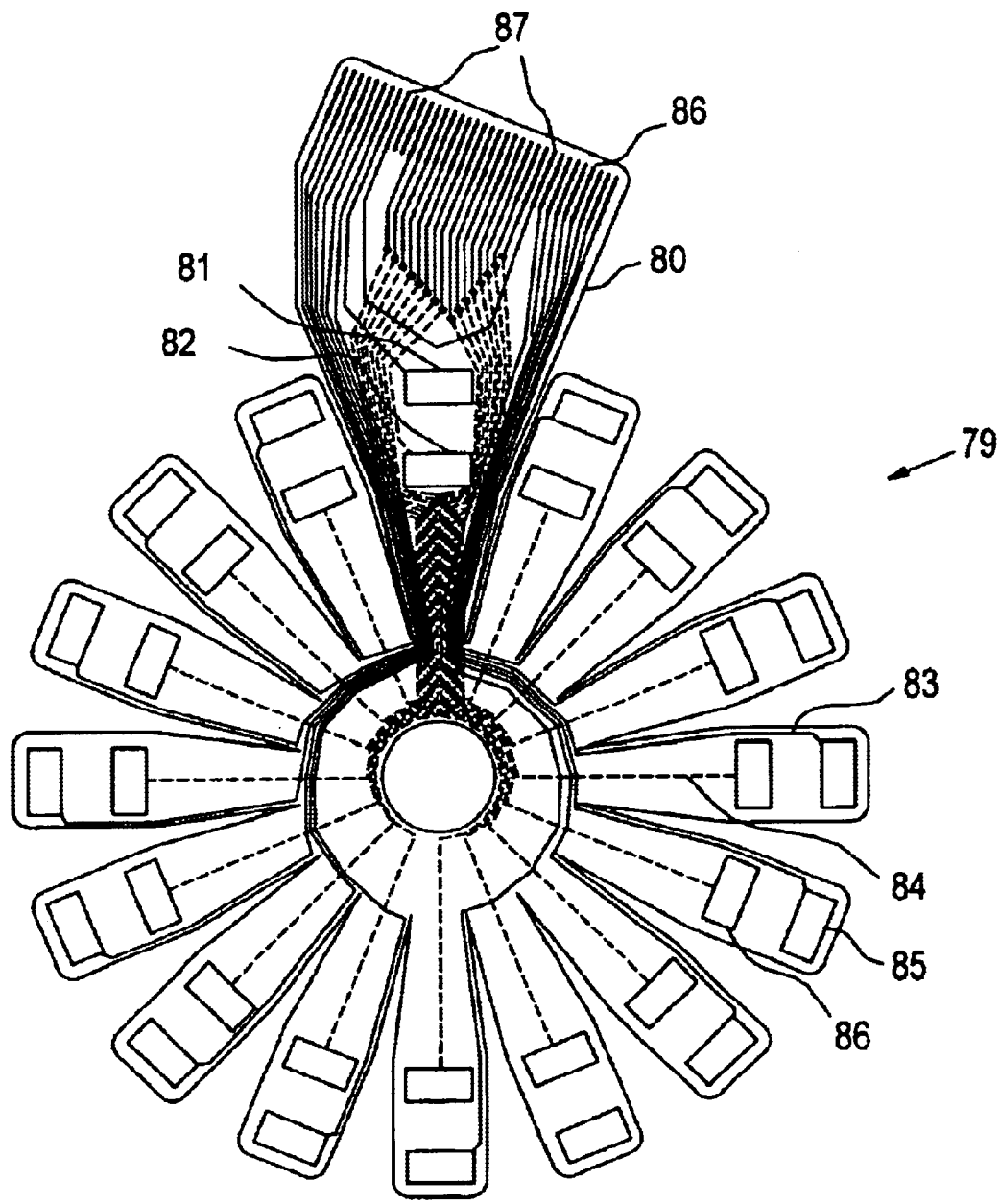
Figure 11A:
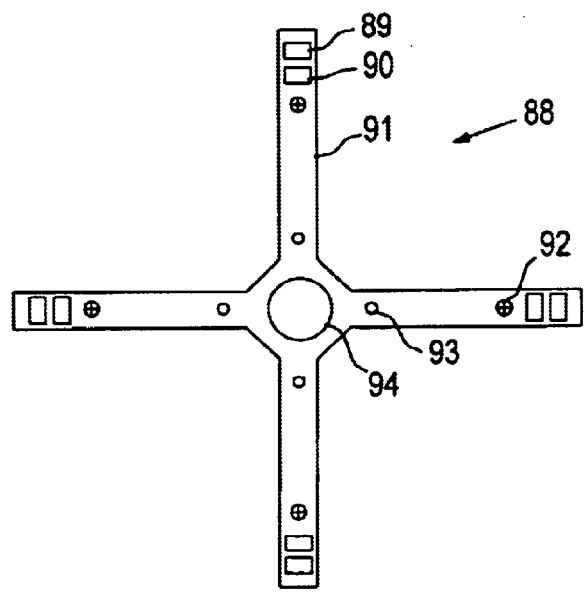
Figure 11B:
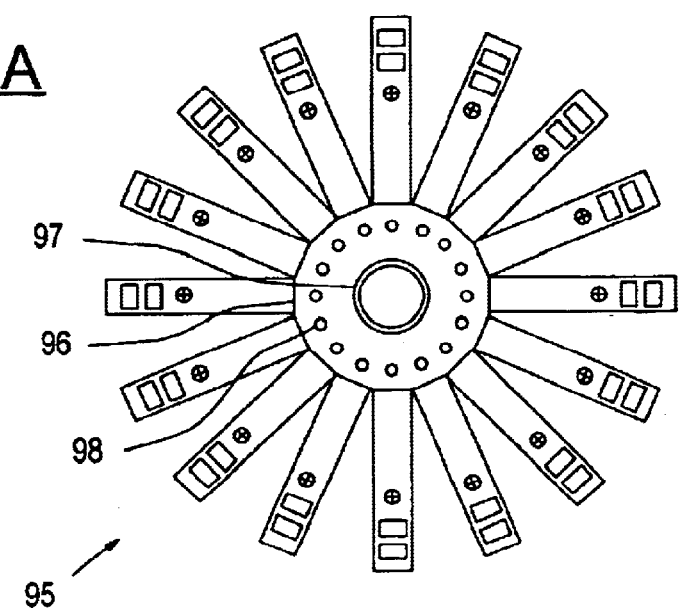
Figure 12:
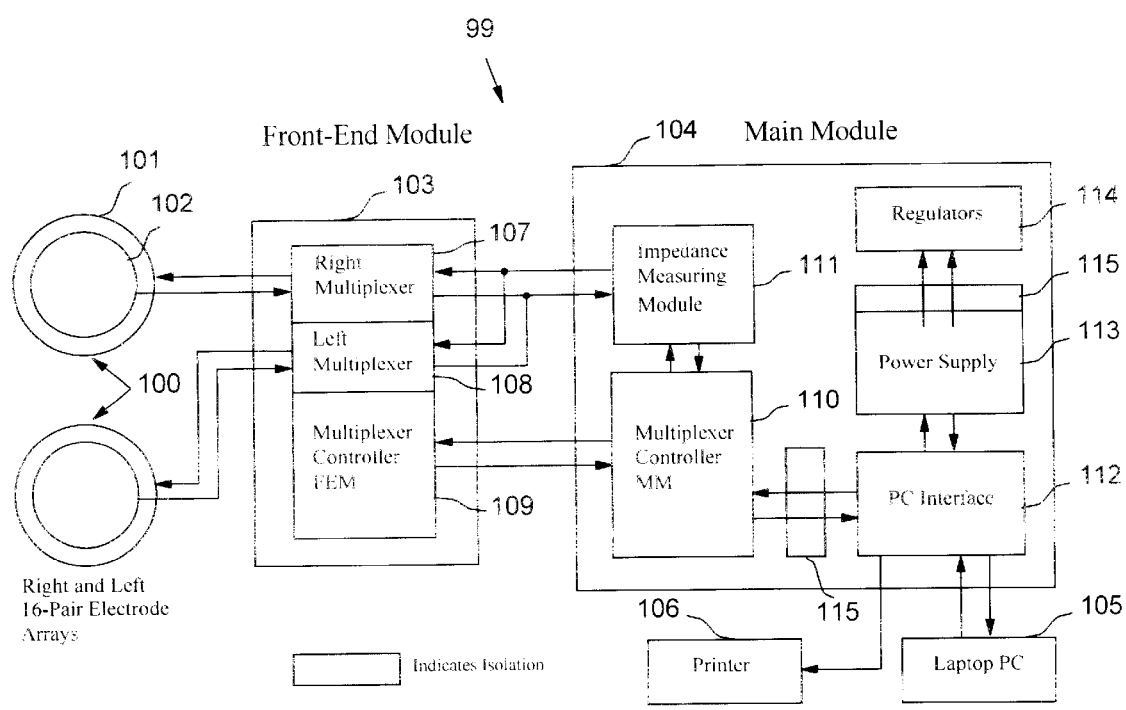
Figure 12A:
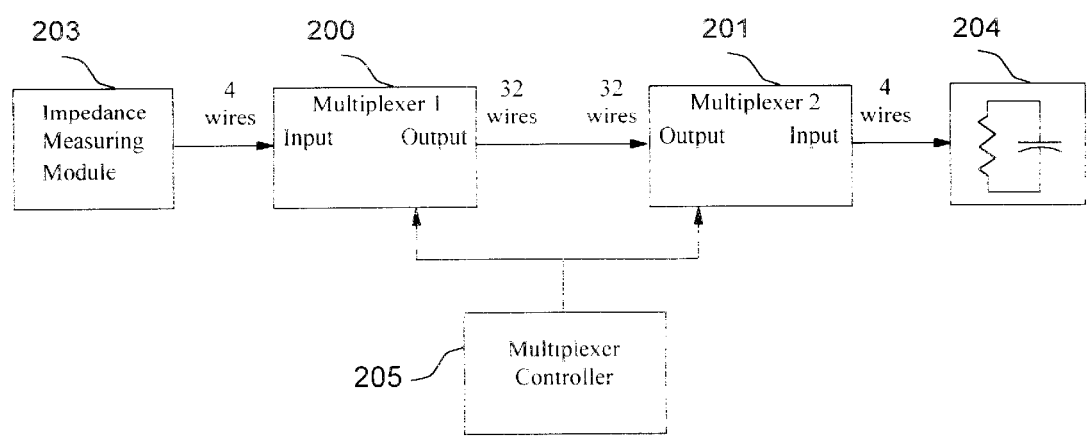
Figure 13A:
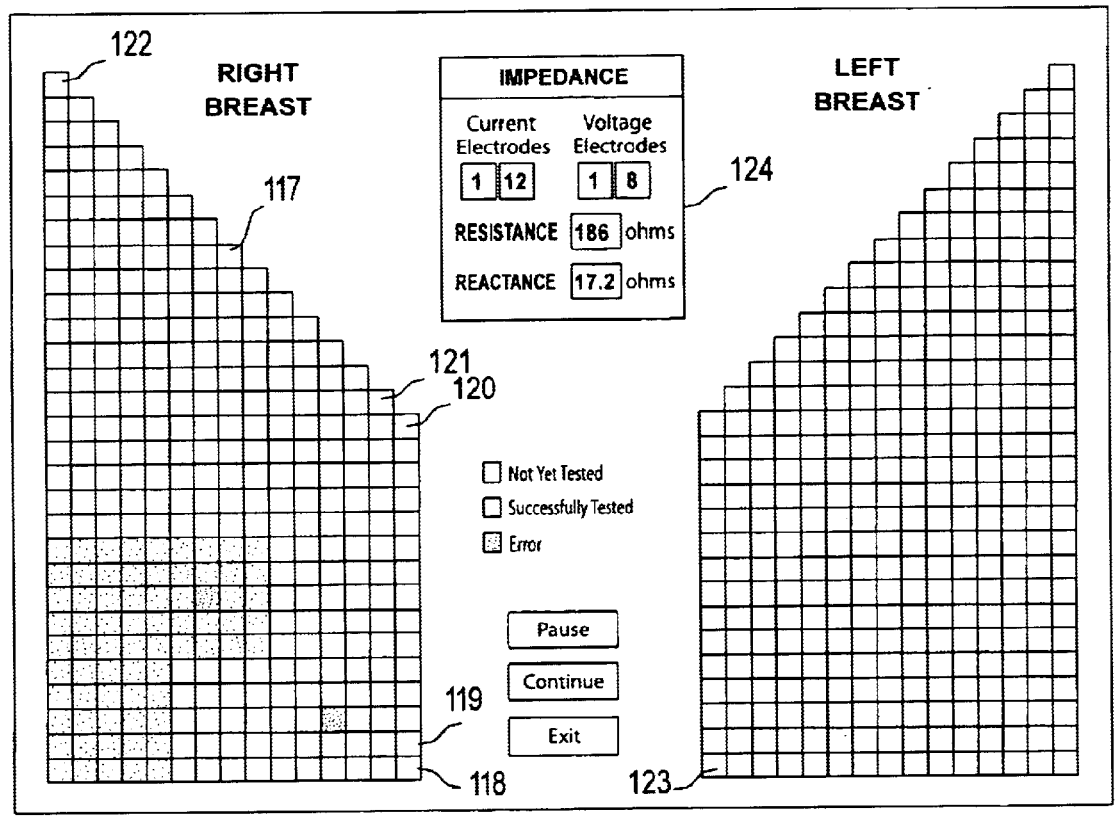
Figure 13B:
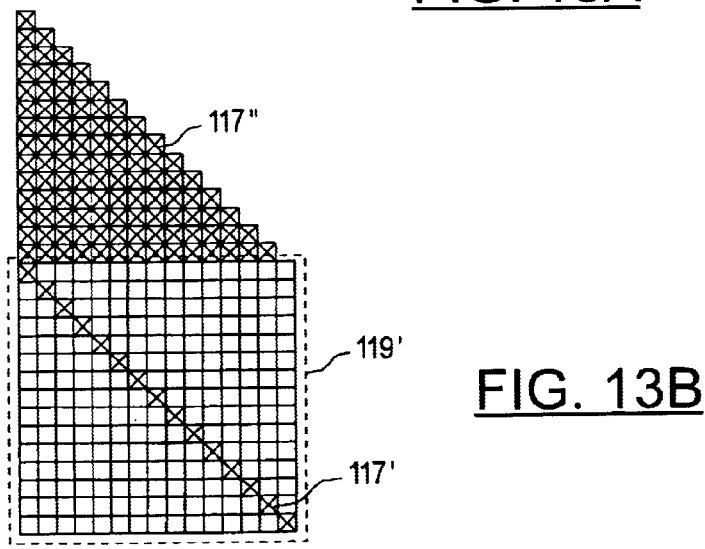
Figure 14:
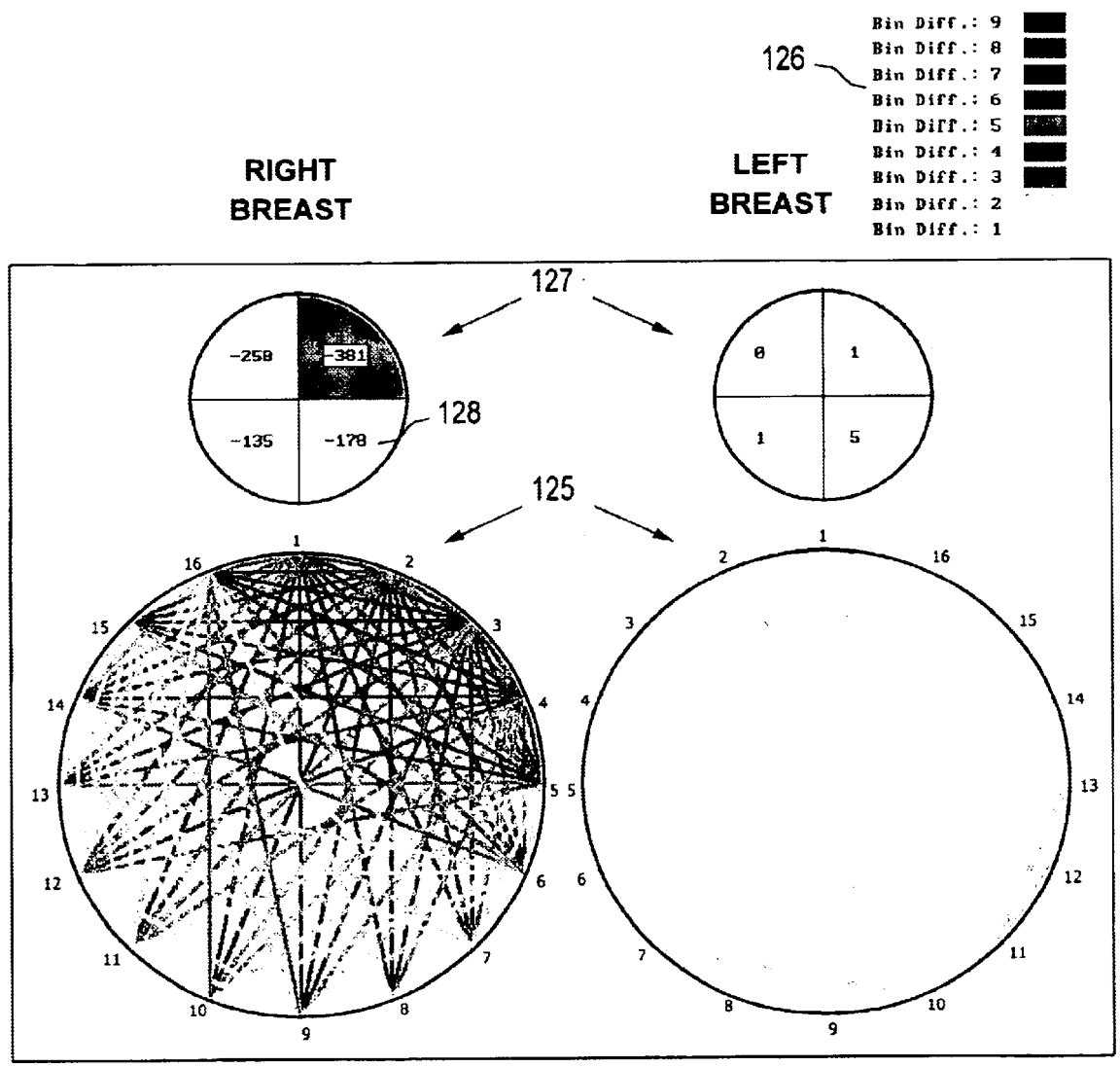
Figures 15A, 15B:
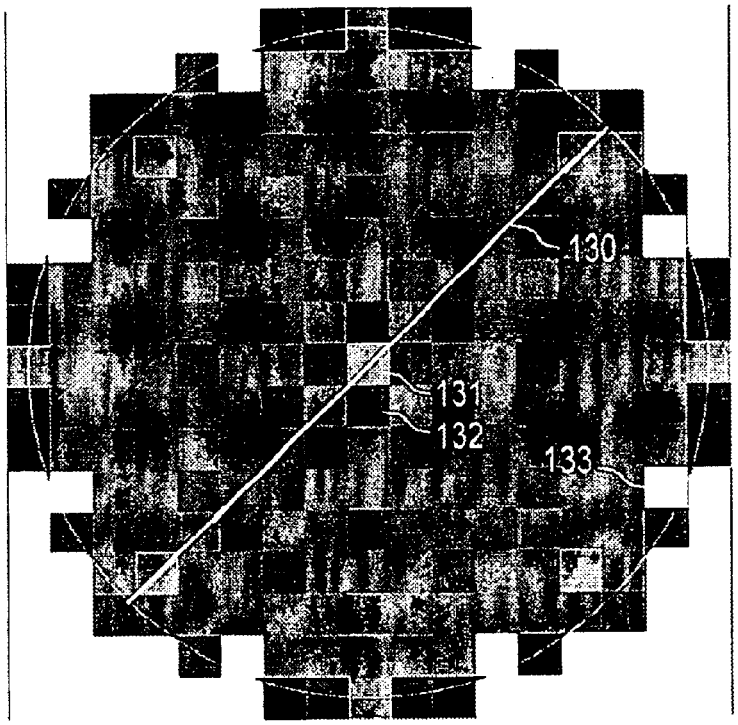
Figure 16A:
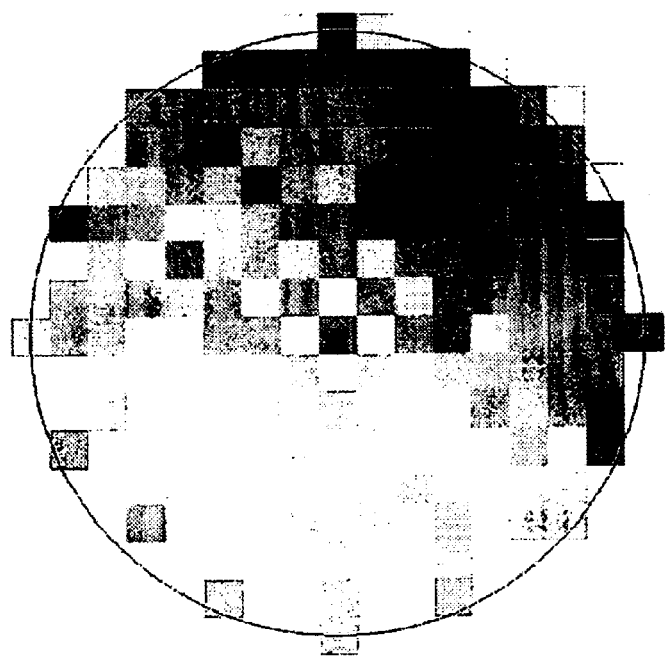
Figure 16B:

FIG. 7B provides detail of the electrical wiring of the flexible ribbon cable of FIG. 7A;

FIG. 8 is an illustration of a three-part cable retainer used for attaching the breast electrode array of FIG. 5 to the flexible ribbon cable of FIG. 7A;

FIG. 9A-1 provides detail of a base part of the cable retainer of FIG. 8;

FIG. 9A-2 is a cross-sectional view of the base part taken along the lines A—A of FIG. 9A-1;

FIG. 9B-1 provides detail of the washer part of the cable retainer of FIG. 8;

FIG. 9B-2 is a cross-sectional view of the washer part taken along the lines B—B of FIG. 9B-1;

FIG. 9C-1 provides detail of another embodiment of the washer part of the cable retainer of FIG. 8;

FIG. 9C-2 is a cross-sectional view of the washer part of FIG. 9C-1 taken along the lines C—C;

FIG. 9D is a sectional view of the breast electrode array connected to the flexible ribbon cable using the three-part cable retainer;

FIG. 9E is an enlarged sectional view of the area indicated as 9E in FIG. 9D, illustrating the compressive action of the base and washer parts of the cable retainer of FIG. 8 against the flexible ribbon cable of FIG. 7A and the breast electrode array of FIG. 5;

FIG. 10 is an illustration of a modification of the breast electrode array of FIG. 5 showing alternative electrical wiring;

FIGS. 11A and 11B illustrate further alternative multi-arm electrode arrays;

FIG. 12 is a block diagram of a data acquisition and analysis apparatus used in the invention;

FIG. 12A illustrates a method of testing the data acquisition and analysis apparatus used in the invention;

FIG. 13A is an illustration of a display screen of the apparatus of FIG. 12;

FIG. 13B provides further detail about the impedance display of FIG. 13A;

FIG. 14 is an illustration of a bin difference chord plot and node counts;

FIG. 15A is an illustration of a tissue impedance distribution shown as a pixel plot, where all tissue impedances have been idealized as being equal;

FIG. 15B is a numerical representation of the pixel values of the plot of FIG. 15A;

FIG. 16A is a pixel impedance difference plot obtained from the same data as used in FIG. 14; and FIG. 16B is a pixel equalized version of the plot of FIG. 16A.

DESCRIPTION OF PREFERRED EMBODIMENT

Electrical Impedance and the Four Electrode Measurement Technique

Electrical impedance is measured by using four electrodes as shown in FIG. 1. The outer pair of electrodes 1 is used for the application of current I, and the inner pair of electrodes 2 is used to measure the voltage V that is produced across a material, such as tissue 3, by the current. The current I flowing between electrodes 1 is indicated by the arrows 4. The impedance Z is the ratio of V to I; i.e., $$Z = \frac{V}{I}.$$

By using separate electrode pairs for current injection and voltage measurement polarization effects at the voltage measurement electrodes are minimized and a more accurate measurement of impedance can be produced.

Impedance consists of two components, resistance and capacitive reactance (or equivalently, the magnitude of impedance and its phase angle). Both components are measured, displayed, and analyzed in the present invention. However, for the purpose of explanation of the invention, only resistance will be used and will interchangeably be referred to as either resistance or the more general term impedance.

Breast Electrode Arrays

FIG. 2 discloses a breast electrode array 5 of the invention that has sixteen electrode pairs, each pair consisting of an outer electrode 8 for current injection and an inner electrode 9 for voltage measurement. To simplify the figure, conductive pathways and electrical connectors are not shown. The illustrated implementation of the array has a main section 6 and a tail section 7. Sixteen pairs of rectangular electrodes in circular orientation are shown, but there are many alternatives that could be advantageously used with the present invention: more or fewer electrode pairs; different electrode shapes and sizes; other shapes for the main body and tail sections of the array; and other geometrical arrangements of the electrodes, e.g., radial sectors with three or more electrodes. Regardless of the electrode arrangement, four electrodes must be used for each impedance measurement, two electrodes between which current is injected, and two electrodes across which voltage is measured. They need not necessarily be physically inner and outer as shown in FIG. 2.

The electrodes 8 and 9 are made of an electrically conductive, self-adhesive material such as a hydrogel so that when the array is positioned on the skin and pressed against it, the adhesive quality of the electrodes assures good skin fixation. Alternatively, adhesive material can be used at various positions on the main section 6 and/or the tail section 7 of the array for fixation of the array. In order to assure impedance is measured in all regions of the breast, electrode arrays 5 are made in different sizes for use in women with different breast cup sizes.

The backing material of breast electrode array 5 must be flexible in all directions (for purposes of illustration a material flexible in all directions is, for example, cotton but not, for example, a material like polyester which when flexed in one direction becomes rigid in the transverse direction) in order to conform to the breast surface and ensure good electrode contact. The backing material must also allow for the deposition of conductive ink to provide the electrical pathways for the electrodes. An example of a material that meets all these requirements is Tyvek® Dupont polyethylene fibre. Shape conformity is further aided by cutouts or darts 11. The darts 11 can be placed at various positions at the inner edge of the main section 6, or the outer edge, or combinations thereof.

Figure 3:
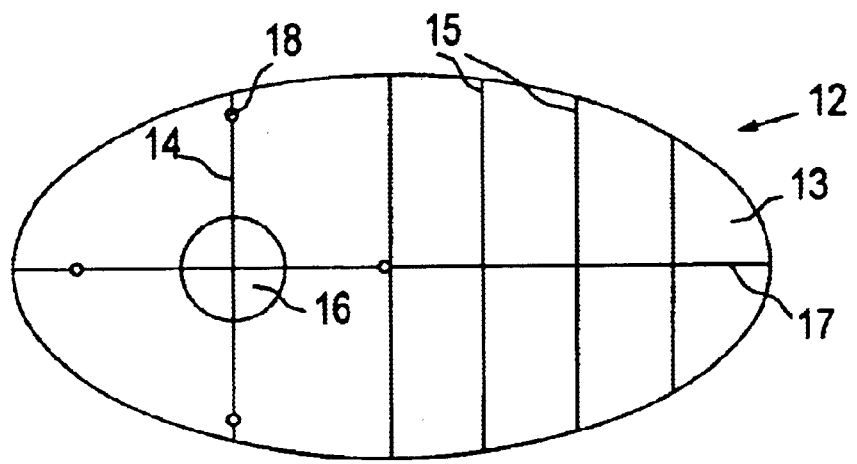
FIG. 3 is an illustration of a positioning template for a breast electrode array.

More accurate and consistently identical placement of electrode arrays on both breasts is aided by positioning the alignment marks 10 shown at four locations on the inner edge of the main section 6 of breast electrode array 5 over alignment marks put on the skin using positioning template 12 having a body made of flexible, transparent material 13, shown in FIG. 3. Placement of these marks is uniquely identified by one point (the centre of the nipple) and one angle or equivalently one axis (the vertical axis of the body). This axis can be identified by using a plumb line while the subject is standing or sitting erect, and marking a vertical axial line on the skin. Template 12 is positioned on the breast with central cutout 16 centered about the nipple. The template is then rotated so that lines 15 are parallel to the marked vertical axis of the body. Providing template 12 with several lines 15 facilitates vertically aligning lines 15 and the marked vertical axis of the body by using one or more of the lines 15 closest to the marked vertical axis of the body. The transparency of template 12 allows its reversal for use on both sides of the body. There are four small holes 18, two on vertical axis 14 and two on horizontal axis 17 which correspond exactly to the alignment marks 10 of breast electrode array 5. An ink or other mark is made on the skin surface through the holes 18 of the positioning template 12. The template is then removed and the electrode array is applied with its alignment marks 10 aligned with the ink marks on the skin.

Figure 4:
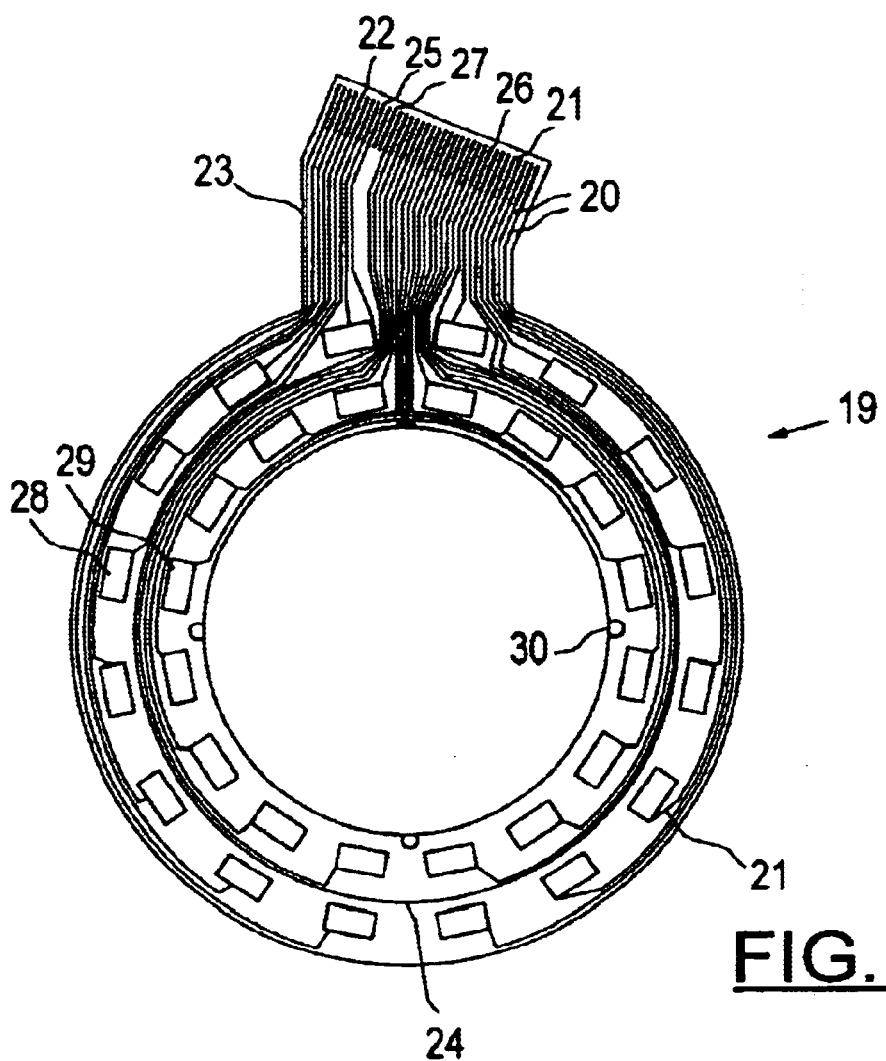
FIG. 4 shows a modification of the breast electrode array of FIG. 2, and an implementation of lead wiring.

FIG. 4 discloses breast electrode array 19, which is a modification of breast electrode array 5 of FIG. 2. FIG. 4 also shows an implementation of electrode lead wiring 20 (conductive paths) and connectors 21, the latter for insertion into a cable attached to the front end electronic module of the invention, to be described later. The darts 11 of breast electrode array 5 are not shown in breast electrode array 19, but they can be beneficially used in the breast electrode array of FIG. 4. The tail section 23 of the breast electrode array 19 can be made angular as shown in FIG. 4 to point inwards toward the body midline in order to facilitate connection to the cable of the front end module that is positioned centrally on the subject or close to the upper mid-chest. Right and left side arrays differ in that their tails 23 are mirror images, each angled appropriately toward the body midline.

Breast electrode array 19 includes a special conductive path, terminating at connectors 25 and 26, to form an electrical ground loop 24. Ground loop 24 improves the isolation of current injection electrodes 28 from voltage measurement electrodes 29. Moreover, ground loop 24 allows for an electrical test to confirm that right and left side arrays have been applied to the correct side. One limb of the ground loop 24 attaches to a terminal for connector 25 on arrays intended for the right breast; this same limb is removed from connector 25 and is attached to a terminal of one of the unused connectors 27 on arrays intended for the left breast. Testing for expected right or left side continuity of the ground loop 24 identifies right and left side arrays.

The array tail 23 may be longer or shorter, angled or straight, of various shapes (e.g., hour glass), and made narrower by reducing the separation of the conductive paths 20 or double-sided printing of the paths 20 with corresponding use of a double sided electrical connector. Alignment marks 30 are used identically to their counterparts 10 in breast electrode array 5 as shown in FIG. 2.

Figure 5A:
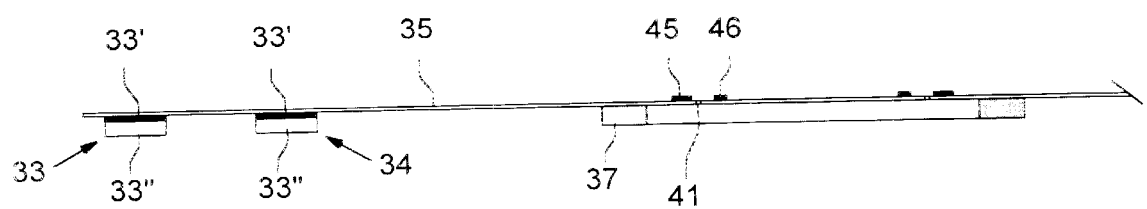
FIG. 5A is a cross-sectional view of the breast electrode array taken along the lines A—A of FIG. 5.

FIGS. 5 and 5A disclose an alternative, preferred breast electrode array 31 of the invention. Sixteen array arms 32 are shown (see FIG. 5), spaced around a body 32'. Each array arm 32 is provided with a current injection electrode 33 and voltage measurement electrode 34. Other embodiments could have fewer arms, or more, narrower arms. The backing material 35 for electrode array 31 is thin, typically about 0.005 inch, is preferentially transparent, and when flexed in one direction becomes relatively inflexible in all other directions. The surface of this material must be printable with conductive ink and accept self-adhesive electrode material such as hydrogels. An example of such a material suitable for this invention is polyester film. The backing material 35 has a central cutout 36 through which cable retainer 62, to be described later, fits. Breast electrode array 31 has a stiffening ring 37, concentric with cutout 36, attached to it. Stiffening ring 37 is flat, about 0.06 inch thick, and is 16-sided. Each of its sides is aligned with the base of an array arm 32. Although not illustrated, the sharp junction 38 between each array arm is preferentially replaced by a small radius cutout to prevent tearing of backing material 35 at that point. Stiffening ring 37 is attached using a suitable adhesive or other means to breast electrode array 31 on the side meant to face the subject's skin. The free side of stiffening ring 37 has an adhesive applied to it so that it, in turn, will attach to the skin. There are a number of alignment marks 39 printed on breast electrode array 31. These marks are matched to erasable markings applied to the breast, using, for example, template 12 as illustrated and discussed in FIG. 3 above, to ensure accurate positioning of the array to each breast. One of the alignment marks 39 has an arrow 40 associated with it to indicate that the axis defined by arrow 40 is to be parallel to the vertical axis of the body. Backing material 35 can also be provided with alignment holes 41 to accept pins of a cable retainer, in a manner to be described.

Figure 6:
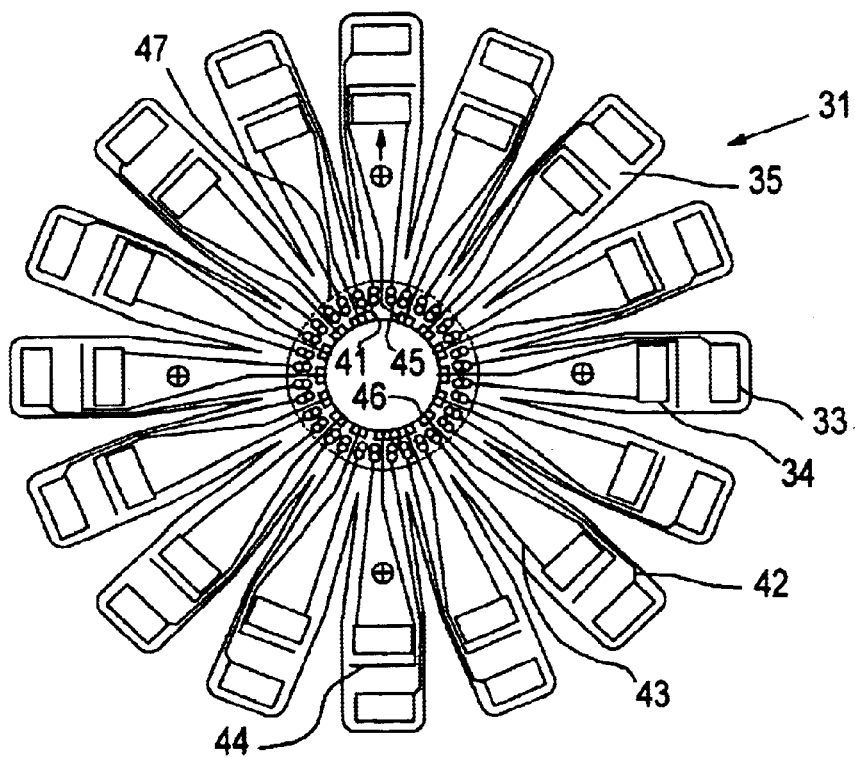
FIG. 6 illustrates electrical wiring of the breast electrode array of FIG. 5.

As illustrated in FIG. 5A current injection electrode 33 and voltage measurement electrode 34 are comprised of two components: a base layer of conductive ink 33' and a conductive adhesive layer 33". One common conductive adhesive is hydrogel, used in applications such as electrocardiography. The hydrogel, which is liquid before it is cured, can be applied to the conductive ink electrode base layer in several ways. One method is to use a hydrogel whose surface tension properties cause it to have a relatively high affinity to conductive ink and low affinity to polyester. As such, the hydrogel can be applied in liquid form where it will distribute evenly over the conductive base layer made the exact size and shape of the electrode. Following application, the hydrogel is cured to solidify. Another method uses adhesive gel foam pads with a cutout of the size and shape of the electrodes. The gel foam pads are applied to the polyester to form a well with the conductive layer as its base. The well is filled with hydrogel, which is then cured. Another method uses solidified, cured sheets of hydrogel that are cut to proper electrode size and shape and applied to the conductive layer base. The non-skin side of backing material 35 has a thin, transparent layer of insulation, covering all of that side of breast electrode array 31 except for an inner circular portion corresponding to the inner diameter 47 (shown as dashed lines) of stiffening ring 37 as shown in FIG. 6. The insulation shields the conductive paths from accidental contact with the subject's skin. The adhesive surfaces of stiffening ring 37 and electrodes 33 and 34 are protected before use by a removable covering with a release liner.

FIG. 6 shows one example of electrical wiring of breast electrode array 31. Conductive paths 42, 43 and 44 are printed on the side of backing material 35 away from the subject's skin (non-skin side). Conductive paths 42 and 43 extend through through-holes (not illustrated) to the side of backing material 35 toward the subject's skin (skin side) to form electrical connections with a generally identical conductive ink that forms the base layer of current injection electrodes 33 and voltage measurement electrodes 34 respectively.

Conductive paths 42 and 43 connect on their other ends to connector tabs 45. There are also 16 ground conductive paths 44, one each positioned between current injection electrodes 33 and voltage measurement electrodes 34 and their conductive paths 42 and 43, to enhance electrical isolation and reduce cross-talk between these circuit elements. Ground conductive paths 44 connect to connector tabs 46. Note the repeating sequence of two adjacent current paths 42 connected to two adjacent connector tabs 45, an intervening ground path 44 connected to its connector tab 46, then two adjacent voltage paths 43 connected to two adjacent connector tabs 45, with the insertion of a ground path between all current and voltage connector tabs 45, results in further reduction of cross-talk between current and voltage circuit sides. The trapezoidal shape of connector tabs 46 serve a special function, as will be described in the following section.

FIG. 7A discloses a flexible, flat ribbon cable pair 48 constructed of separate ribbons 49 and 50 each of which contain 34 conductive paths, not shown in the figure, that terminate on one end at connector tabs 51 and 52 of the circular connector rings 53. These rings have a central cutout 54 whose diameter is identical to substantially that of central cutout 36 of breast electrode array 31. The conductive paths of ribbons 49 and 50 terminate at their other end at separate rows of a standard two-row, 72-pin connector 55, which in turn attaches to a mating connector of a front-end electronic module of the invention, to be described later. As is standard practice for the manufacture of flexible circuits, the ribbons 49 and 50 are polyimide material, copper is used for the conductive paths, and connector tabs 51 and 52 are copper with a tin/lead coating. Each ribbon 49 and 50 has its thirty four conductive paths printed in standard double-sided manner. Sixteen of the conductive paths serve current injection electrodes, sixteen serve voltage measurement electrodes, and two conductive paths connect to electrical ground, although in general more ground connections could be used. Both surfaces of ribbons 49 and 50 are insulated with a thin polyimide layer 56 except for an inner uninsulated portion of connector rings 53 defined by a diameter 57 at the outside edge of connector tabs 51.

FIG. 7B provides detail of the electrical wiring of connector ring 53 and the adjacent portion of ribbon 49 or 50. Double-sided printing of conductive paths is indicated by solid lines 58 for one side and dashed lines 59 for the other side. One conductive path terminates in each connector tab 51. However, there are only two connections 60 made by conductive paths with ground connector tabs 52, leaving the remaining 14 ground connector tabs 52 to be connected in a manner to be described in the following section. Ribbons 49 and 50 can also be provided with alignment holes 61, as indicated in the figure, to accept alignment pins of a cable retainer, as described below. Two alignment holes 61 are indicated in FIG. 7B but more could be used. The position of such alignment holes could be different for ribbons 49 and 50 to provide a method of detection and/or prevention of reversal of an electrode array, or right-left electrode array interchange.

A connector member is disclosed for attaching the breast electrode array 31 to each of the flexible ribbons 49 and 50. The connecting member comprises a retaining member to receive the electrode array and the flexible ribbons in electrical contact with respect to one another, and a clamping member to clamp the electrode array and flexible ribbons together and secure the electrical contact therebetween. In the embodiment illustrated in FIG. 8 the connector member is cable retainer 62. Cable retainer 62 has three components: a base part 63, a washer 64, and a fastening nut 65. These components are fabricated from a material such as, for example, Delrin® Dupont acetyl copolymer because of its strength, stiffness, hardness, dimensional stability, and electrically non-conductive properties. Other materials, with a similar combination of properties, could also be used. Base part 63 consists of a flat annular flange 66 and a central, hollow, threaded cylindrical tube 67. Annular flange 66 has, on its surface, two concentric ridges 68 and two alignment pins 69. These pins can be fabricated from a material such as Delrin® or a metal such as stainless steel. More detail of base part 63 is shown in FIGS. 9A-1 and 9A-2 where the same identification numbers as in FIG. 8 apply. As particularly shown in FIG. 9A-2 ridges 68 have tapered sides that facilitate alignment with matching and preferably tapered channels, such as channels 70 of washer 64 as illustrated in FIG. 9B-2.

Washer 64, as illustrated in FIGS. 9B-1 and 9B-2 has two circular channels 70 and two alignment holes 71. An alternative embodiment of washer 64 is washer 72, illustrated in FIGS. 9C-1 and 9C-2. In this embodiment washer 72 has two circular ridges 73 and 74 that form with the main body of washer 72 a channel-like formation, and two alignment holes 75. As illustrated in FIG. 9C-1 the outer ridge, ridge 73, is higher than the inner ridge, ridge 74.

The third component of cable retainer 62 of FIG. 8 is fastening nut 65. It has a knurled knob 76, flange 77, and interior thread 78.

FIG. 9D shows an assembled breast electrode array 31, flexible ribbon cable 48, and cable retainer 62 with its base part 63, washer 72, and fastening nut 65.

In operation, breast electrode array 31 is connected to the flexible ribbon cable pair 48 as follows. The threaded cylindrical tube 67 of base part 63 of cable retainer 62 is inserted into the central cutout 36 of breast electrode array 31 from the skin side of the array, the side that has the attached stiffening ring 37, with alignment pins 69 of base part 63 inserted through alignment holes 41 of breast electrode array 31. The diameter of annular flange 66 of base part 63 is slightly less than that of the inner diameter of stiffening ring 37 and the height of annular flange 66 is less than that of the stiffening ring in order to ensure that stiffening ring 37 makes contact with the skin of the breast. At this point, the protective adhesive covering of stiffening ring 37 can be removed and breast electrode array 31, containing base part 63 within it, is centered about the nipple. Before stiffening ring 37 is pressed into firm contact with the skin, breast electrode array 31 is brought into correct rotational alignment. This is accomplished by directing arrow 40 of alignment mark 39 (see FIG. 5) upward toward the head, then superimposing all alignment marks 39 directly over the skin markings previously applied with the aid of a positioning template such as template 12 described in FIG. 3. Optionally, the assembly of the breast electrode array to the flexible ribbon cable can be completed before the array is attached to the breast.

Connector ring 53 of flexible ribbon cable 48 is then slipped onto cylindrical tube 67 of base part 63 so that the following conditions are satisfied: (1) the exposed electrode tabs 51 and 52 of connector ring 53 face electrode tabs 45 and 46 of breast electrode array 31; (2) alignment holes 61 of the connector ring 53 engage alignment pins 69 of base part 63; and (3) flexible ribbon cable 48 is oriented such that 72-pin connector 55 is directed toward the subject's head. Satisfying these conditions will cause electrode tabs 51 of connector ring 53 to fully overly electrode tabs 45 of breast electrode array 31 and cause trapezoidal electrode tabs 52 of connector ring 53 to be staggered with and slightly overlap trapezoidal electrode tabs 46 of breast electrode array 31 making a continuous electrical path. This aspect of the invention has two features. Firstly, since electrode tabs 46 and 52 form a continuous electrical path between the two ground connections 60, shown in FIG. 7B, only two ground conductive paths are required. Secondly, it provides an electrical test of proper application of connector ring 53 to breast electrode array 31 because any application other than the correct one, will cause a break (open circuit) in the continuous electrical path and indicate, as well, that electrode tabs 51 of connector ring 53 are not aligned correctly with electrode tabs 45 of breast electrode array 31. Choice of size, shape, and degree of overlap of mating electrodes tabs 46 and 52 establishes the desired degree of rotational misalignment sensitivity, and measuring the resistance of the conductive paths serving these electrode tabs could also be used to provide an indication of the degree of misalignment and the contact pressure. Other implementations of this technique are possible by varying the number and pattern of missing connections to ground electrode tabs, then relying on establishing a ground connection circuit that requires correct rotationally staggered alignment of ground electrode tabs on connector ring 53 and breast electrode array 31.

Following the attachment of connector ring 53 to cylindrical tube 67 of base part 63, washer 72 and fastening nut 65 are, in turn, applied to cylindrical tube 67. Washer 72 is rotated so that its alignment holes 71 engage into alignment pins 69 of base part 63, thereby preventing rotation of washer 72. Moreover, washer 72 (or washer 64) alone, or in combination with flexible ribbon cable 48 and breast electrode array 31, is of a height at least as great as that of alignment pins 69, as shown in FIGS. 9D and 9E. Fastening nut 65 can then be turned to bring washer 72 firmly into contact with connector ring 53. In this manner, electrode tabs 51 and 52 of connector ring 53 are brought in contact with electrode tabs 45 and 46 of breast electrode array 31. This contact is secured by the effects of the compressive force against the flexible polyimide material of connector ring 53 and the flexible polyester of breast electrode array 31 as they are clamped between the ridges 68 of base part 63 and the complementary ridges 73 and 74 of washer 72, or alternatively the complementary channels 70 of washer 64. The compressive force bends the flexible substrates causing them to act in the manner of a dish spring in which the ridges 68 of base part 63 are the fulcrum points of a circular bent beam as illustrated in FIG. 9E. This action also produces a desirable contact wiping action of the electrode tabs as the flexible substrates assume a slight dish shape under compression. The contacting surfaces of the washer and the fastening nut of cable retainer 62 can be designed with matching bumps on one part and holes on the other, or staggered bumps on both surfaces, to provide tactile and audible guides to the degree of compression. Locking of bumps into holes, or abutment of surface bumps, could also provide additional assurance against unscrewing.

Once breast electrode array 31 is connected to the flexible ribbon cable 48 in a correct orientation, and attached to the breast by the adhesive material on stiffening ring 37, attachment of all electrodes 33 and 34 can proceed accurately and reproducibly. In particular, the action of stiffening ring 37, which is flat, is to force the skin of the attached breast into the same, flat plane. Therefore, each array arm 32, as it originates from a straight side of stiffening ring 37 will, as it is gently pressed radially outward, easily flex and conform to the contour of the breast surface, while at the same time the arm becomes rigid and inflexible along any other direction but its radial contour because of the nature of the polyester film, as previously described. The application process is completed by pressing and attaching self-adhesive electrodes 33 or 34 at the end of each array arm 32 (once their protective covering has been removed) to the skin in a true radial position. The combination of these features—the flattening of the skin by the stiffening ring, the design of a many sided stiffening ring to provide each array arm with a straight axis around which to flex, the preferred bending of the array material in its initial direction of flexing as the array arm conforms to the breast surface, and conversely its rigidity in all other directions—all ensure consistent inter-electrode spacing (equal in the example used), and reproducible, accurate side-to-side electrode positioning, all necessary conditions for the meaningful use of homologous electrical impedance analysis as described in this invention.

FIG. 10 discloses breast electrode array 79, a modification of breast electrode array 31, that shows alternative electrical wiring. In this modification one of the array arms has been widened and elongated to form a connecting tail section 80 similar to that of breast electrode array 19 of FIG. 4. The positions of current injection electrode 81 and voltage measurement electrode 82 have not been changed to maintain, in this instance, the identical geometrical pattern of all electrodes as in breast electrode array 31. Widening of the array arm allows conductive paths 83 and 84, from the remaining fifteen pairs of current injection electrodes 85 and voltage measurement electrodes 86 respectively, to be routed in connecting tail 80 along with conductive paths serving electrodes 81 and 82. Double-sided printing of conductive paths is indicated by solid lines for one side and dashed lines for the other side. All conductive paths terminate at connectors 86 and, in general, all the features attributed to tail section 23 of FIG. 4, such as the use of ground connectors 87 for confirmation of correct right and left side breast electrode array placement, are equally applicable here. The use of ground conductive paths for improved isolation of current injection and voltage measurement circuit sides, although not shown, could be implemented either as intervening conductive paths and/or areas of conductive ink.

FIGS. 11A and 11B disclose an alternative method of effecting multi-arm electrode arrays. In particular FIG. 11A discloses a basic four-arm electrode array 88. It has conventional adhesive hydrogel current injection electrodes 89 and voltage measurement electrodes 90 on thin, transparent polyester film. Each arm 91 of the array has alignment marks 92 and alignment holes 93. There is a central cutout 94 that in use is centered about the nipple. For simplicity of illustration, electrical wiring is not shown. Other basic arrangements, with fewer or more arms, combinations of different length arms, and arms equally or unequally rotated from one another, could be used to create various sized and shaped electrode arrays. In addition, there could be three or more electrodes on each arm 91 to measure impedance radially or in other geometric configurations.

FIG. 11B shows a plan view, electrode side, of the assembly of four of the four-arm electrode arrays 88 into a sixteen-arm electrode array 95. Electrode arrays 88 are held together by engaging their cutouts 94 over the threaded hollow cylinder 97 (bottom only can be seen) of array retainer 96, rotating them into predetermined positions by further engagement of their alignment holes 93 with alignment pins 98 (bottom only can be seen) of array retainer 96, followed by clamping with a washer and nut over threaded hollow cylinder 97. The bottom of array retainer 96 is similar to stiffening ring 37 in that its bottom surface is generally flat and stiff with an adhesive covering for providing initial attachment of the assembly to the skin. For reasons stated for stiffening ring 37 of breast electrode array 31, array retainer 96 forces the skin surface attached to it into a flat plane. Correct positioning of electrode array 95 on the breast is obtained by overlying its alignment marks 92 with ink marks placed on the skin with a positioning template, as previously described.

In general, electrodes in various disclosures herein have been depicted as rectangular, and electrode pairs positioned side-by-side. A number of other configurations could beneficially be used, including electrodes of various shapes including but not limited to circular, ovoid, annular, and C-shaped. Current injection and voltage measurement electrodes need not be of similar shape, nor be the same size or be side by side. For example, a C-shaped voltage measurement electrode and a small, circular current injection electrode positioned between the open ends of the C-shaped voltage measurement electrode may have advantages of size and effectiveness.

Impedance Data Acquisition

FIG. 12 discloses a block diagram of the data acquisition and analysis apparatus 99 for automatically measuring, processing and analyzing impedance data. For the purposes of illustration, the apparatus 99 will be described as employed for screening, locating and diagnosing breast cancer. However, it should be recognized that the method and apparatus of the invention could be employed in a similar manner for screening or diagnosis at other body sites and for other conditions and diseases. Breast electrode arrays 100 have, for this example, sixteen pairs of electrodes as in the preferred breast electrode array 31 of FIG. 5. As previously described, the four electrode technique is used to measure electrical impedance (or its reciprocal, admittance). A continuous 50 kilohertz sine wave current of constant amplitude I is applied between two current injection electrodes in the outer circumference 101 of an electrode array, and the resultant voltage V is measured between two voltage measurement electrodes in the inner circumference 102 of the electrode array. The positioning of current electrodes in an outer circumference, and voltage electrodes in an inner circumference is not exclusive for the invention; many other arrangements and configurations of electrodes could be used. Use of a 50 kilohertz sine wave is standard practice for many bioimpedance applications, but there is an extended range of useable frequencies and, to a lesser degree, other waveforms. Impedance Z is calculated from $$\frac{V}{I}.$$

As will be described later, with the illustrated embodiment, three hundred and thirty such impedance values are obtained (scanned) for each breast.

Apparatus 99 has as its major components front-end module 103, main module 104, and laptop PC 105. There is also a printer 106 for a hard copy of reports and results. Within front-end module 103 there is a right multiplexer 107 and a left multiplexer 108. These multiplexers provide connections to the right and left breast electrode arrays respectively. For each measurement, four connections are made at a time, two to current injection electrodes in outer circumference 101 of a breast electrode array and two to voltage measurement electrodes in inner circumference 102 of the same array. As presently performed, all three hundred and thirty measurements are completed on one side before the measurement process begins on the other side. There are many other possibilities so long as only one side is activated at a time; for example, a routine could be followed that alternated between a single measurement on one side, then the homologous measurement on the other side. The selections of the four connections for measurement are given by multiplexer controller for the front-end module (multiplexer controller FEM) 109 that provides digital address control to right and left multiplexers 107 and 108.

There are five sub-modules 110 to 114 within main module 104. The current invention discloses a multiplexer controller main module (multiplexer controller MM) 110 with a 12-bit counter and three EEPROM chips that contain blocks of words (i.e, "memorized" electrode selection patterns, such as, for the illustrated embodiment, the sequence and pattern illustrated in FIG. 13, as discussed below) used primarily for front-end module multiplexer electrode selection and control. Using a multiplicity of words from the EEPROM chips activated rapidly by the 12-bit counter, multiplexer controller MM enables the three hundred and thirty impedance measurements to be completed quickly (less than thirty seconds in the present invention). Operation of impedance measuring module 111 is controlled generally by laptop PC 105 by RS232 signals through its serial port. PC interface board 112 connects to both the serial and parallel ports of laptop PC 105. The parallel port is used for general control of power supplies and communication with multiplexer controller MM 110. In the example provided both the serial and parallel ports of laptop PC 105 are used. Consequently, PC interface board 112 has a serial port duplicator to provide connection to printer 106. Regulated power to the various sub-modules is supplied by power supply 113 and regulators 114. Electrical isolation is obtained at isolation interfaces 115 by optocouplers and, at power supply 113, by dc-to-dc voltage conversion.

The present invention discloses a method by which two identical multiplexers can be tested by reversely operating one of them. FIG. 12A shows an example of two identical multiplexers, multiplexer 200 and multiplexer 201, generally functioning to switch four wires at their inputs to a multiplicity of combinations of four of the thirty two wires available at their outputs. To perform the test, the outputs of the multiplexers are connected together. Multiplexer 201, which is reversely operated, has its four inputs connected to calibration load 204, here a simple RC network. As multiplexer controller 205 simultaneously controls the multiplicity of output selections of the multiplexers, the impedance of calibration load 204 is read by impedance measuring module 203 at the input of multiplexer 200. For proper multiplexer operation, the load value measured must remain constant and equal to the calibration load for all multiplexer output combinations. If this is not so, then at least one of the multiplexers is not functioning properly and needs repair. Since front end module 103 of the present invention contains identical right and left multiplexers, apparatus 99 can be configured and switched as required into a multiplexer test mode as described.

An electrode array numbering convention has been established in which electrode pairs are numbered clockwise one to sixteen for the right breast, with the uppermost electrode pair numbered one, and counterclockwise in similar fashion for the left breast so that mirror-imaged electrode pairs will always be compared. Current and voltage electrode pairs are functionally single electrodes, so if each pair is considered as one of n electrodes, then the number of impedance measurements required between such electrodes to obtain a matrix of impedance values is (n−1)×(n−1). Therefore, a set of 15×15=225 measurements are required for a sixteen (pair) electrode array. This set is obtained as follows: Current is applied between the outer electrodes of electrode pairs 1 and 2 and then, in turn, the voltage between the inner electrode of electrode pair 1 and all other inner electrodes are measured, i.e., $V_{1,2}$, $V_{1,3}$ ... $V_{1,16}$. Dividing each of these voltages by $I_{1,2}$, the current between outer the electrodes of electrode pairs one and two, gives the first fifteen impedance values. Current is next applied between the outer electrodes of electrode pairs one and three, $I_{1,3}$, which will create a new pattern of electric field potentials. Then, the voltage is again measured between the inner electrode of electrode pair 1 and all other inner electrodes ($V_{1,2}$, $V_{1,3}$ ... $V_{1,16}$). Dividing each of the voltages by $I_{1,3}$ gives the next fifteen impedance values. This process is repeated for current applied between the outer electrodes of electrode pairs one and four, one and five, . . . , one and sixteen, to produce, finally, fifteen sets of fifteen impedance values. Placing these impedance values (elements) in a fifteen-row by fifteen-column grid results in an impedance matrix.

There is a special subset of fifteen impedance values in the 225 element set—those that use the same pair of electrodes for current injection and voltage measurement; for example, current $I_{1,13}$ applied between the outer electrodes of electrode pairs 1 and 13, and voltage $V_{1,13}$ measured between inner electrodes of the same electrode pairs gives impedance $$Z = \frac{V_{1,13}}{I_{1,13}}$$

Impedances in this subset are called $Z_{same}$ type impedances. They are indicated by $Z_{1,2}$, $Z_{1,3}$, ... $Z_{1,16}$. There is additional value, as will be disclosed later under Data Analysis, in measuring all other possible $Z_{same}$ impedances, as listed below:

$$
\begin{array}{cccccc}
Z_{2,3} & Z_{2,4} & Z_{2,5} & & \cdots & Z_{2,16} \\
& Z_{3,4} & Z_{3,5} & Z_{3,6} & \cdots & Z_{3,16} \\
& & Z_{4,5} & Z_{4,6} & Z_{4,7} & \cdots & Z_{4,16} \\
& & & & \cdots & \\
& & & Z_{13,14} & Z_{13,15} & Z_{13,16} \\
& & & & Z_{14,15} & Z_{14,16} \\
& & & & & Z_{15,16}
\end{array}
$$

Therefore, a complete set of impedance measurements for one breast, when a sixteen pair electrode array is used, consists of two hundred and twenty five measurements for the impedance matrix, and another one hundred and five measurements to obtain all values for $Z_{same}$, resulting in a total of three hundred and thirty impedance measurements for each breast. This number will, of course, change as electrode number changes. The process of selecting lead sets and obtaining these measurements is called an impedance scan.

FIG. 13A discloses a method in a single display screen 116 of laptop PC 105 of real-time monitoring of acquisition of impedance data, reviewing any of the 660 impedance values obtained (i.e., 330 measurements for each breast), and displaying the occurrence of measurement errors. Each of the 330 impedance measurements for the right and left breasts is represented by a pixel 117, here depicted as a square, but not limited to this form. As further illustrated by the outline square 119' of FIG. 13B, the bottom 15×15 pixels on either side are the two hundred and twenty five measurements used to form the impedance matrix. Included in this, on the diagonal of the square, are fifteen $Z_{same}$ measurements, indicated at 117' by squares with an "X." The sloping top section 117" represents the remaining one hundred and five $Z_{same}$ measurements (filled with an "X") needed to complement the fifteen $Z_{same}$ values within the impedance matrix. Initially, all pixels in FIG. 13A are blank. As each value is obtained, first for the right breast, pixels fill in starting at the lower right corner pixel 118, and then continue to fill in the bottom row from right to left (this row represents current injected between electrodes one and two, and voltage measured between one and two, one and three, . . . , one and sixteen). Pixel 119, at the next row higher is filled next, then the process continues as this row is filled from right to left (this row represents current injected between electrodes one and three, and voltage measured between one and two, one and three, . . . , one and sixteen). The process is repeated until the fifteenth row, starting with pixel 120, has been completed (this row represents current injected between electrodes one and sixteen, and voltage measured between one and two, one and three, . . . , one and sixteen). These two hundred and twenty five pixels, as noted above, represent the impedance matrix. Filling in continues in similar manner for the remaining one hundred and five $Z_{same}$ measurements, starting with pixel 121, filling in from right to left, until the 330$^{th}$ pixel 122 is filled. Real time error checking of measurement is performed for factors such as consistency and fit within a range of expected values, and errors are indicated dynamically at their associated pixels during the filling process. Shading or color coding is used to differentiate those pixels (measurements) with successful measurements from those detected with errors. The entire process, including error checking, takes less than 30 seconds.

Since both breast electrode arrays are applied before testing, impedance measurement and consequently pixel filling begins for the left breast virtually immediately after the right breast is completed. Filling proceeds in a mirror image of the sequence for the right breast, starting at pixel 123 in the lower left corner, then running along rows from left to right. The display is made to unfold in this manner to convey a sense of homologous side-to-side measurement. Upon completion of the impedance scan, any measurement can be reviewed in window 124 by bringing the arrow cursor over its corresponding pixel and clicking. The window indicates the current injection and voltage measurement electrodes used, and displays the values of resistance and reactance. Pixels corresponding to any measurements that, according to the error-detecting algorithms of the invention are inconsistent or outside of expected limits for either normal or diseased tissue (generally determined by clinical data), are indicated by color or shading, here as black. Bringing the arrow cursor over such a pixel and clicking will display a window with a text message indicating the electrode(s) likely responsible for the problem.

Data Analysis (A) The Difference Impedance Matrix

The breast can be considered as a non-homogeneous, electrically conducting object with M+1 electrode pairs (to be referred to in this discussion simply as an "electrode," one that can be used for both current injection and voltage measurement without electrode polarization). One electrode is assigned as the reference electrode with zero potential. The current at the reference electrode is the sum of the currents that are applied to the other M electrodes. The impedance matrix Z relates the currents $I_i$, the current through the ith electrode, and the voltages $V_i$, the potential difference between the ith electrode and the reference electrode, where i=1, 2, 3, . . . , M, is as follows:

$$
\begin{bmatrix} V_1 \\ V_2 \\ V_3 \\ \vdots \\ V_M \end{bmatrix} = Z \times \begin{bmatrix} I_1 \\ I_2 \\ I_3 \\ \vdots \\ I_M \end{bmatrix}
$$

which can be condensed as V=Z×I.

For an object with M+1 electrodes as described above, the impedance matrix Z is defined as an M×M matrix:

$$
Z = \begin{bmatrix}
Z_{11} & Z_{12} & Z_{13} & \cdots & Z_{1M} \\
Z_{21} & Z_{22} & Z_{23} & \cdots & Z_{2M} \\
Z_{31} & Z_{32} & Z_{33} & \cdots & Z_{3M} \\
\vdots & \vdots & \vdots & \vdots & \vdots \\
Z_{M1} & Z_{M2} & Z_{M3} & \cdots & Z_{MM}
\end{bmatrix}
$$

Each matrix element $Z_{ij}$ (i,j=1, 2, 3, . . . , M) is equal to $$\frac{V_i}{I_j}$$

when all currents except the current at the jth electrode are equal to zero. In a given subject, the impedance matrix Z is unique for a given pattern of breast electrodes and therefore represents the "signature" of the breast. Associated with certain types of matrices, including the impedance matrices as structured in the present invention, are characteristic values called eigenvalues, and characteristic vectors called eigenvectors. They are characteristic in the sense that by mathematical analysis each 15×15 impedance matrix, in the present example, can be represented by a set of fifteen numbers, i.e., fifteen eigenvalues, that are unique to that matrix. Furthermore, associated with each eigenvalue is a unique 15D vector, its eigenvector. Since the eigenvalues and eigenvectors characterize the matrix, and impedance is sensitive to tissue changes resulting from disease, the present invention uses eigenvalues and eigenvectors as a means of detecting and diagnosing disease states. This is applicable to either a Z matrix, or R and $X_c$ matrices, if Z is resolved into its resistive and capacitive reactive components respectively. The number of eigenvalues and eigenvectors available for this purpose will vary with the size of the impedance matrix, increasing as the number of electrodes used in the array becomes larger.

A method of using the 15×15 impedance matrix for diagnosis is now disclosed. It is based on homologous matrix comparison between the right and left breasts by obtaining an Absolute Difference Matrix (ADM) and a Relative Difference Matrix (RDM). In order to calculate the ADM, the matrix with lower mean impedance (or R or $X_c$) value is identified, as it is the side more likely to have malignant cells. The ADM is obtained by subtracting element-by-element the impedance matrix with the lower mean value from the matrix with the higher mean value. The Relative Difference Matrix is obtained by calculating relative differences between the two matrices element-by-element. The resulting matrices (ADM and RDM) can be characterized and used in the following ways for diagnosis assuming that clinical studies using these methods have established statistically significant norms and thresholds:

(1) By calculating the ADM and RDM matrix norm (a standard mathematical method of characterizing magnitude of matrix elements with a single number). A norm higher than a pre-established threshold is an indicator of a malignant tumor in the breast with the lower mean impedance value.

(2) By calculating the ADM and RDM matrix determinant. A determinant higher than a pre-established threshold is an indicator of a malignant tumor in the breast with the lower mean impedance value.

(3) By obtaining the sum of all the elements in an ADM and RDM. A sum higher than a pre-established threshold is an indicator of the malignant tumor in the breast with the lower mean impedance value.

(4) With a 2D plot showing sums of elements in ADM (or RDM) columns. This will provide information regarding the location of the tumor because columns with higher values indicate a higher probability of the tumor being in the vicinity of the corresponding electrode.

(5) With a 3D matrix plot showing the absolute (in the case of ADM) or relative (in the case of RDM) difference magnitudes as a function of the location of the element in the matrix.

(B) Sum of ALGEBRAIC Bin Differences

The present invention can also use the special set of impedance values, referred to previously as $Z_{same}$, as a means of detecting and diagnosing disease states. This set, for a sixteen pair electrode array, has 120 elements (see FIG. 13). Homologous $Z_{same}$ impedance measurements (and all other Z measurements) for normal subjects have some minor differences because there are always small anatomic or physiologic side-to-side differences. These normal variations, however, do not mask larger differences that result when one side is affected by a disease that changes its electrical properties. One method of analysis in the present invention uses a metric, known herein as Sum of Algebraic Bin Differences (SABiD). The SABiD is obtained as follows. The minimum and maximum values of the two hundred and forty $Z_{same}$ impedance measurements (one hundred and twenty per side) are used to define the impedance range for that subject, then the range is subdivided into twelve (or other number of) equal, smaller sized ranges called bins. Bins for the present invention are numbered one to twelve, and the two hundred and forty impedance values are assigned the bin number into whose range they fall. The numbering system is specified such that bin one contains the lowest impedance values, proceeding through to bin twelve that contains the highest impedance values. The algebraic bin difference is then taken between each of the one hundred and twenty homologous $Z_{same}$ sites. Since the location of a cancer will not, in general, be known, a convention is established wherein the left bin number is subtracted from the right bin number. The one hundred and twenty algebraic bin difference values are added to give SABiD. The presence of a cancer in a breast will cause a decrease in impedance of some quantity of $Z_{same}$ measurements on that side. This will manifest as correspondingly lower bin numbers for that side and therefore greater bin differences. Greater bin differences will add to give a larger SABiD value. A SABiD value higher than a pre-established threshold is an indicator of a malignant tumor. The pre-established threshold is generally determined by clinical data comparing the ranges of SABiD values from subjects with no breast disease to the range of SABiD values from subjects with diagnosed breast disease. Expressing impedance values by their bin number normalizes them and validates intersubject comparison of SABiD. Using the convention for subtraction indicated, the SABiD value will be negative for tumors in the right breast, and positive for tumors in the left breast.

An alternative method of bin allocation is the use of minimum and maximum of the one hundred and twenty $Z_{same}$ impedance values for each side, thereby defining the impedance range, and the limits of each bin, separately for each side. Bins are again numbered one to twelve in our example, and the one hundred and twenty impedance values on each side are assigned the appropriate bin numbers related to their side. Calculation of SABiD then proceeds as before.

(C) Sector Node Counts

Breasts can be represented as circles (or other encircling loci) in the frontal plane, and the $Z_{same}$ impedances between electrode pairs drawn as chords of the circle at the positions of the electrode pairs. Impedance magnitudes are assigned bin numbers. However, since a basis of the detection method disclosed herein is homologous comparison between right and left breasts, a preferred plot would indicate these differences. Therefore bin numbers for homologous chords are compared, subtracting the bin number of the chord from the right breast from the bin number of its homologous match in the left breast. If the bin numbers are equal, no chord is plotted; if they are different, the chord is plotted on the side that has the lower bin number. The bin differences will be negative for plots in the right breast, and positive for plots in the left breast, according to the right side minus the left side convention adopted. A bin difference chord plot 125 for a sixteen-pair electrode array is shown in FIG. 14. Bin differences 126 are color coded in shades of grey with the smallest difference, labelled "Bin Diff.: 1", the lightest shade and the largest bin difference, labelled "Bin Diff.: 9", shown as black. The data used to construct this plot are representative of changes occurring with a cancer in the upper inner quadrant of the right breast. As indicated above, by following increasingly darker shades, the eye is led to areas of larger bin differences that are produced by the lower impedance of neoplastic cells; in this case, the upper inner quadrant. It is again emphasized that this is not an image of the structure of the underlying breast, and indeed the complexity and impracticality of attempting to construct impedance images are purposely avoided. Instead, a multiplicity of impedance measurements are obtained from precisely homologous sites in the left and right breasts, and differences only are graphically represented using the concept of bin difference chords.

The present invention discloses the use of sector node counts (displayed at 127), as a numerical indicator of breast cancer location that improves upon the visualization offered by chord plots. This method of analysis starts with a bin difference chord plot and considers each electrode voltage/current pair as a node that has a given number of chords converging on it. Counting the total number of chord convergences at a node is weighted in the following manner. A count of one is added at the node for all its convergent chords with bin difference one, a count of two is added at the node for all its convergent chords with bin difference two, and so on for higher bin difference chords, to give a final sum as the count of weighted convergences at that node. In the example of FIG. 14 the circular breast representation is divided into quadrants, although the number of sectors could be increased for greater spatial definition. For a 16 pair array, there are five nodes per quadrant, including the border nodes (border nodes appear twice in the count, i.e., in adjacent quadrants). Adding the node counts for the five included nodes gives a total node count for that quadrant (for example, −178 for quadrant 128). The quadrant with the highest node count indicates the tumor location, here the upper inner quadrant of the right breast. Node count sign is according to the right minus left side subtraction convention noted above.

(D) Pixel Impedance Displays and Pixel Equalization

Another disclosure of the present invention reveals an effective and reliable method for displaying the distribution of tissue impedance, in the described example, in the frontal plane from data such as the one hundred and twenty $Z_{same}$ values obtained from sixteen pairs of electrodes uniformly distributed along the circumference of a circle. The display method is based on digitization of the circular region into a 17×17 pixel grid (spatial resolution) as shown in FIGS. 15A and 15B. Eight-bit (256 levels) shading or coloring is used for intensity resolution. Assuming equal distribution of the measured impedance along each chord, and recognizing that there will be different lengths of a chord (chord segment) within various pixels, and different numbers of chords through various pixels, the impedance intensity or value for a pixel can be calculated. A display of all such pixels is a pixel impedance plot. Pixel impedance plot (PIP) 129 of FIG. 15A is a special case in which all $Z_{same}$ values have been made identical. The large variation in pixel intensity in PIP 129 demonstrates that since the total contribution of chords to various pixels is not uniform, a method for pixel equalization is necessary. As noted, a chord segment is the length of a chord within the boundaries of a pixel. For example, chord 130 of PIP 129, between electrode pairs three and eleven, passes through thirteen pixels, of which the first and last pixels have small chord segments and the other 11 pixels have equal and larger segments. The larger cord segments are, in fact, the diagonals of the pixels, which is the longest possible length within the square. If a unit square is assumed, then the diagonal segment is the square root of 2=1.414. Therefore chord 130 contributes 1.414 chord segments to each of the eleven pixels through which it passes. Other chords, to varying degrees, pass through these same eleven pixels, contributing chord segments to each pixel to give the total chord segments for a given pixel. With the sixteen pair electrode model the maximum total chord segments for any pixel is 12.44 and the minimum is 0.014. These values are derived from equations that give, for each chord, its chord segment contribution to each pixel, then summing the total chord segments for each pixel. For digital 8-bit visualization a scale factor of 20.50 (255/12.44) is used to map the range of 0 to 12.44 to 0 to 255. This changes the value for the maximum total chord segments from 12.44 to 255 (12.44×20.50) and the minimum from 0.014 to 0.287 (0.014×20.50). In FIG. 15A a grey scale is used, with 0 total chord segments assigned black and 255 total chord segments assigned white.

FIG. 15B gives a numerical version 134 of PIP 129 in which the value of each pixel is shown (recall that impedance values are equal). The values in FIG. 15B have had the scale factor of 20.50 applied to them. If the boundary pixels (the pixels that are partially inside and partially outside of the circle) are not considered, then the maximum total chord segments occur at pixel 131 at the centre of PIP 129, and equals for this example where all $Z_{same}$ values are identical, 187. The minimum occurs at the four pixels 132 beside centre pixel 131, each with value of 53. The highest pixel total chord segment value (255) occurs at the eight boundary pixels 133 that are partially inside and partially outside the circle. The reason for this relates to the large number of chords passing through the eight boundary pixels and the relatively long chord segments falling inside them. Even allowing for the fact that 10.5% of boundary pixels 133 lie outside the circle, the adjusted value of 228 remains the largest one. Dividing a pixel impedance plot by the data of FIG. 15B results in an equalized pixel impedance plot. Equalizing PIP 129 produces equally shaded pixels throughout, thereby reflecting the true pixel impedance values.

Since the present invention uses side-to-side homologous comparison of $Z_{same}$ data to diagnose disease, pixel difference impedance plots can be constructed by subtracting homologous pixel values, right side minus left side (maintaining the convention previously used) then plotting the pixel difference on the side with the lower pixel value. This is termed an algebraic difference PIP. An unequalized algebraic difference PIP 135 is shown in FIG. 16A. This plot is of the right side only, and was obtained using the same data as for FIG. 14; i.e., data reflecting a cancer in the upper inner quadrant of the right breast. In pixel difference plots, the grey scale is coded so that zero pixel difference is assigned white and maximum pixel difference, which is scaled to 255, is assigned black. FIG. 16B shows a pixel equalized version 136 of the algebraic difference PIP 135, to demonstrate the resultant improvement in clarity with which homologous impedance differences can be delineated and localized.

As an alternative to subtracting homologous pixel difference (algebraic difference), a relative homologous pixel difference such as:

$$\frac{\text{(value right side} - \text{value left side)}}{\text{(smaller value)}}$$

can be calculated, equalized, and plotted, as previously described, and is referred to as a relative difference PIP.

The range of pixel impedance difference can be scaled with a scale factor, derived separately for algebraic difference PIPs and for relative difference PIPs. The respective scale factors are derived from the greatest observed pixel difference (algebraic or relative) observed in a large sample population, such that the difference when scaled would have the maximum intensity level of 255. Therefore, any other subject's pixel differences would have lesser levels when scaled, thereby allowing valid, consistent intersubject comparison of impedance differences.

Even though the foregoing development used 2-dimensional plotting of equalized pixel difference impedance plots, a strength of the technology is that 3-dimensional impedance differences are revealed because of the natural 3-dimensional flow of current in volume conductors. It is as if each pixel is a window to localized impedance changes in a volume of tissue extending beyond its plane.

(E) Sum of Algebraic Pixel Differences (SAPiD)

Two metrics, sum of algebraic pixel differences (SAPiD) and sector pixel counts, analogous to SABiD and sector node counts from the impedance bin difference method, can be obtained. SAPiD is the sum of homologous algebraic pixel differences of equalized right and left PIPs, pixel by corresponding homologous pixel, and serves the same function as SABiD; i.e., a SAPiD value higher than a pre-established threshold (generally determined by clinical data) is an indicator of a malignant tumor and, using the convention for subtraction indicated previously, the SAPiD value will be negative for tumors in the right breast, and positive for tumors in the left breast. The dynamic range, and therefore the probable diagnostic usefulness, of the SAPID metric is much larger than that of SABiD. The latter generally uses up to a 16-level bin; for SAPiD, 256 levels are easily used.

(F) Sector Pixel Counts

An indication of tumor location is provided by using either algebraic difference or relative difference PIPs, and summing pixel values in each sector, usually quadrants of a circle in conformity with mammography practice. For purposes of this application, this is called the sector pixel count. The quadrant with the highest sector pixel count gives the probable location of the tumor, given that SAPiD exceeds a pre-established threshold. Sector pixel counts use equalized data, and therefore can be expected to more accurately locate a tumor than sector node counts. Sector pixel counting may be performed in delineated areas of the circle other than its sectors to "focus in" on a suspicious area, much in the same way magnification views of suspicious areas are taken in X-ray mammography.

The concepts of pixel impedance plots, pixel equalization, pixel difference impedance plots, sum of algebraic or relative pixel differences, and sector pixel counts have been disclosed using as illustration impedance data obtained from 16 pairs of electrodes uniformly distributed in a circle, and digitization of the circular region into a 17×17 pixel grid. These disclosures apply as well to data obtained from greater (or lesser) numbers of electrodes, the use of larger number of pixels for greater spatial resolution, more levels of pixel shading or coloring (e.g., 12-bit or 16-bit) for higher intensity resolution, and to non-uniformly distributed electrodes that may be arranged in circular or other geometrical configurations.

It can appreciated that variations to this invention would be readily apparent to those skilled in the art, and this invention is intended to include those alternatives.

We claim:

1. A method of diagnosing the possibility of a disease state in one of first and second substantially similar parts of a living organism, the method comprising:

a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;

b) identifying the set with a lower mean impedance value;

c) arranging each of the first and second sets in respective mathematical matrices;

d) creating an absolute difference matrix by subtracting each measurement of the set with the lower mean impedance value from the corresponding measurement of the other set; and e) analyzing the absolute difference matrix to diagnose the possibility of a disease state.

2. A method according to claim 1 wherein the absolute difference matrix is used to calculate a matrix norm that is compared to a pre-established threshold to diagnose the possibility of a disease state.

3. A method according to claim 1 wherein the absolute difference matrix is used to calculate a matrix determinant that is compared to a pre-established threshold to diagnose the possibility of a disease state.

4. A method according to claim 1 wherein a sum of all of the values in the absolute difference matrix is calculated and compared to a pre-established threshold to diagnose the possibility of a disease state.

5. A method according to claim 1 wherein a visual display for diagnosing the location of a disease state is provided by summing the values in each of the absolute difference matrix columns and representing these sums in a bar graph.

6. A method according to claim 1 wherein a visual display for diagnosing the possibility of a disease state and a location thereof is provided by plotting the value of each element in the absolute difference matrix as a function of the location of the element in the matrix.

7. A method of diagnosing the possibility of a disease state in one of first and second substantially similar parts of a living organism, the method comprising:

a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;

b) arranging each of the first and second sets arranged in respective mathematical matrices;

c) creating a relative difference matrix by calculating the relative differences between each measurement from the first set with the corresponding measurement of the second set; and d) analyzing the relative difference matrix to diagnose the possibility of a disease state.

8. A method according to claim 7 wherein the relative difference matrix is used to calculate a matrix norm that is compared to a pre-established threshold to diagnose the possibility of a disease state.

9. A method according to claim 7 wherein the relative difference matrix is used to calculate a matrix determinant that is compared to a pre-established threshold to diagnose the possibility of a disease state.

10. A method according to claim 7 wherein a sum of all of the values in the relative difference matrix is calculated and compared to a pre-established threshold to diagnose the possibility of a disease state.

11. A method according to claim 7 wherein a visual display for diagnosing the location of a disease state is provided by summing the values in each of the relative difference matrix columns and representing these sums in a bar graph.

12. A method according to claim 7 wherein a visual display for diagnosing the possibility of a disease state and its a location thereof is provided by plotting the value of each element in the relative difference matrix as a function of the location of the element in the matrix.

13. A method of diagnosing the possibility of a disease state in one of first and second substantially similar parts of a living organism, the method comprising:
  a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;
  b) calculating an impedance range by subtracting the minimum impedance measurement from either of the first and second sets from the maximum impedance measurement from such sets;
  c) creating a plurality of numbered bins by subdividing the impedance range into smaller range sizes then numbering the smaller range sizes consecutively;
  d) assigning a bin number to each of the impedance measurements from the first and second sets;
  e) creating a bin difference set by subtracting the bin number of each impedance measurement from one of the first and second sets from the bin number of each corresponding impedance measurement of the other set; and
  f) calculating a sum of all of the bin difference values in the bin difference set and comparing to a pre-established threshold to diagnose the possibility of a disease state.

14. A method of diagnosing the possibility of a disease state in one of first and second substantially similar parts of a living organism, the method comprising:
  a) obtaining a plurality of impedance measurements across predetermined portions of each of the parts to produce first and second sets of impedance measurements, the first set for the first part and the second set for the second part, and wherein each measurement of the first set has a corresponding measurement in the second set when taken across corresponding portions of each of the parts;
  b) calculating a first impedance range for the first set by subtracting the minimum impedance measurement from the maximum impedance measurement of that set, and calculating a second impedance range for the second set by subtracting the minimum impedance measurement from the maximum impedance measurement of that set;
  c) creating a plurality of first numbered bins by subdividing the first impedance range into a first set of smaller range sizes then numbering the first set of smaller range sizes consecutively, and creating a plurality of second numbered bins by subdividing the second impedance range into a second set of smaller range sizes then numbering the second set of smaller range sizes consecutively;
  d) assigning one of the first bin numbers to each of the impedance measurements from the first set, and assigning one of the second bin numbers to each of the impedance measurements from the second set;
  e) creating a bin difference set by subtracting the bin number of each impedance measurement from one of the first and second sets from the bin number of each corresponding impedance measurement of the other set; and
  f) analyzing the bin difference set to diagnose the possibility of a disease state.

15. A method according to claim 14 wherein a sum of all of the bin difference values in the bin difference set is calculated and compared to a pre-established threshold to diagnose the possibility of a disease state.

16. A method of diagnosing the possibility of a disease state in one of first and second substantially similar parts of a living organism, the method comprising:
  a) obtaining a plurality of impedance measurements taken between a predetermined plurality of points encircling the parts to produce first and second sets of impedance measurements, the first set for the first part and the second set for the second part, and wherein each measurement of the first set has a corresponding measurement in the second set when taken between a corresponding plurality of points;
  b) assigning a bin number to each of the impedance measurements from the first and second sets;
  c) producing a bin chord plot for each of the parts by graphically depicting the plurality of points as nodes in an encircling path for each part and the impedance measurements taken between the plurality of points as a bin chord extending between the respective nodes;
  d) dividing each graphical depiction into sectors; and
  e) analyzing the bin chords that converge on a given node within a sector to diagnose the possibility of a disease state.

17. A method according to claim 16 wherein each sector graphically displays the total number of bin chords that converge on all the nodes included within that sector.

18. A method according to claim 16 wherein the difference between corresponding bin chords for each part is plotted as a bin difference chord on the graphical depiction for the part having a lower bin number.

19. A method according to claim 18 wherein the calculation of the number of bin difference chords that converge on a given node is weighted depending on the differences between bin numbers from the first set and corresponding bin numbers from the second set.

20. A method according to claim 19 wherein each sector graphically displays the total number of bin difference chords that converge on all the nodes included within that sector.

21. A method according to claim 16 wherein the bin numbers are created by subdividing an impedance range obtained by subtracting the minimum impedance measurement from either of the first and second sets from the maximum impedance measurement from such sets into smaller range sizes then numbering the smaller range sizes consecutively.

22. A method according to claim 16 wherein the bin numbers are created by subdividing a first impedance range obtained by subtracting the minimum impedance measurement from the maximum impedance measurement of the first set of impedance measurements into a first set of smaller range sizes then numbering the first set of smaller range sizes consecutively, and by subdividing a second impedance range obtained by subtracting the minimum impedance measurement from the maximum impedance measurement of the second set of impedance measurements into a second set of smaller range sizes then numbering the second set of smaller range sizes consecutively.

23. A method of diagnosing the possibility of a disease state in one of first and second substantially similar parts of a living organism, the method comprising:

a) obtaining a plurality of impedance measurements taken between a predetermined plurality of points encircling the parts to produce first and second sets of impedance measurements, the first set for the first part and the second set for the second part, and wherein each measurement of the first set has a corresponding measurement in the second set when taken between a corresponding plurality of points;

b) producing a pixel grid from a chord plot produced by the impedance measurements taken between the plurality of points; and c) analyzing the pixel grid to diagnose the possibility of a disease state.

24. A method according to claim 23 wherein the intensity of a pixel in the pixel grid is determined from the chords that pass through the pixel.

25. A method according to claim 24 wherein the number of chords, the impedance value of a chord, and the size of a chord segment that passes through the pixel are used in determining the intensity of the pixel.

26. A method according to claim 25 wherein the intensity of the pixels in the pixel grid is equalized to account for differences in the number of chords and the size of chord segments that pass through the various pixels to produce a pixel grid wherein pixel intensity indicates impedance value only.

27. A method according to claim 26 wherein the impedance intensity of the pixels is displayed visually.

28. A method according to claim 27 wherein the visual display of the impedance intensity of the pixels is generated by a computer to produce a plurality of levels to represent different levels of intensity.

29. A method according to claim 28 wherein the visual display generated by the computer has 256 levels to represent different levels of intensity.

30. A method according to claim 28 wherein the pixel grid is a pixel difference plot derived by subtracting corresponding impedance pixels from the plurality of points of the first part and the second part.

31. A method according to claim 28 wherein the pixel grid is a pixel difference plot derived by calculating the relative difference between corresponding impedance pixels from the plurality of points of the first part and the second part.

32. A method according to claim 30 or 31 wherein a constant, pre-established scale factor is applied to the impedance intensity of the pixels.

33. A method according to claim 30 or 31 wherein the pixel grid is divided into sectors and each sector graphically displays the sum of the impedance intensities for all pixels that are within the sector.

34. A method according to claim 26 wherein a pixel difference set is obtained by subtracting the pixel impedance value from one of the first and second sets from the pixel impedance value from each corresponding impedance measurement of the other set and the pixel difference set is analyzed to diagnose the possibility of a disease state.

35. A method according to claim 24 wherein a sum of all of the pixel difference values in the pixel difference set is calculated and compared to a pre-established threshold to diagnose the possibility of a disease state.

36. A method according to claim 34 wherein the pixel difference set is a pixel algebraic difference grid obtained by subtracting corresponding pixel impedance values taken between the plurality of points of the first part and the second part.

37. A method according to claim 34 wherein the pixel difference set is a pixel relative difference grid derived by calculating the relative difference between corresponding impedance values taken from the plurality of points of the first part and the second part.

38. A method according to claim 36 or 37 wherein the pixel grid is divided into sectors with each sector graphically displaying a sum of the impedance values for all pixels within that sector.

* * * * *